United States Patent [19]
Sharpless et al.

[11] Patent Number: 5,994,583
[45] Date of Patent: Nov. 30, 1999

[54] TWO STEP SYNTHESIS OF D- AND L- α-AMINO ACIDS AND D- AND L- α-AMINO-ALDEHYDES

[75] Inventors: K. Barry Sharpless; Guigen Li, both of La Jolla, Calif.

[73] Assignee: The Scripps Research Institute, La Jolla, Calif.

[21] Appl. No.: 08/651,228

[22] Filed: May 22, 1996

[51] Int. Cl.$^6$ .................................................. C07C 229/04
[52] U.S. Cl. .......................................... 562/575; 562/553
[58] Field of Search ..................................... 568/704, 705; 564/356; 562/575, 553

[56] References Cited

U.S. PATENT DOCUMENTS 4,871,855  10/1989  Marko .

OTHER PUBLICATIONS

CA:8941984 Abs Gazz Chim Ital 107 (9–10),Paiaro, pp. 467–472, 1977.
CA:118169412, ab s of WO9220677, Nov. 1992.
CA:122:9606, Sharpless, Tetrahedron Asymmetry 5 (8), pp. 1473–1476, 1994.
CA121;179066, Tetrahedron lettm 35(29) Sharpless, pp. 5129–5132, 1994.
CA:76:45490, Marken, Dissertation Univ Microfilms Ann Arbor Mich Order NO 41–21, 176, 1972
CA:80:59624, Ohgo, Chem lett. (1) pp. 33–36, 1974.
CA:124:29604, abs of WO9517386, Jun. 1995.
CA:78:123587, ABS of J Amer Chem, 95 (5), Noyori, pp. 1674–1676, 1973.
CA:110:172656 abst of "Convenient synthesis of vicinal diamines", Jones, J Org Chem 54(8) pp. 1940–1943, 1989.
CA:109:230851 abst of "Palladium catalyzed intramolecular aminocarbonylation" Tamaru, J Org Chem 53(24) pp. 5731–5741, 1988.

*Primary Examiner*—Paul J. Killos
*Assistant Examiner*—Jean F Vollano
*Attorney, Agent, or Firm*—Donald G. Lewis

[57] ABSTRACT

D- and L-α-amino acids and D- and L-α-amino aldehydes are synthesized from olefin substrates in two steps. The first step is a catalyzed asymmetric aminohydroxylation addition reaction to the olefin substrate. The addition reaction is catalyzed by osmium and is co-catalyzed by chiral ligands. The chiral ligands, in addition to being co-catalysts with the osmium, also serve to direct the addition reaction regioselectively and enantioselectively. Divalent ligands are preferred over monovalent ligands because of their enhance regio- and enantio-selectivity. As an oxidant nitrogen source for the addition reaction, either a carbamate or sulfonamide may be employed. If carbamate is employed as an oxidant nitrogen source, the resultant β-hydroxycarbamate is deprotected to yield the corresponding β-hydroxyamine. If sulfonamide is employed as an oxidant nitrogen source, the resultant β-hydroxysulfonamide is deprotected to yield the corresponding β-hydroxyamine. The resultant β-hydroxyamine is then selectively oxidized in a second synthetic step to produce the desired D- and L-α-amino acid or D- and L-α-amino aldehyde.

10 Claims, 8 Drawing Sheets

R = CF$_3$-, CH$_3$, -CH$_2$CH$_2$CH$_2$-NH-C(=NH)-NH$_2$, -CH$_2$C(=O)NH$_2$

-CH$_2$COOH, -CH$_2$SH, -CH$_2$CH$_2$COOH, -CH$_2$CH$_2$CONH$_2$,

-CH$_2$(CH$_3$)CH$_2$CH$_3$, -CH$_2$CH(CH$_3$)$_2$, -CH$_2$CH$_2$CH$_2$CH$_2$-NH$_2$

-CH$_2$CH$_2$SCH$_3$, -CH$_2$CH$_2$CH$_2$-NH$_2$, -CH$_2$-OH, -CH$_2$(OH)CH$_3$,

-CH(CH$_3$)$_2$,

TWO STEP SYNTHESIS OF D- AND L- α-AMINO ACIDS AND D- AND L- α-AMINO-ALDEHYDES

FIELD OF INVENTION

The invention relates to the synthesis of D- and L-α-amino acids and D- and L-α-amino aldehydes from olefins and other unsaturated substrates. More particularly, the invention relates to a two step synthesis in which the first step is an asymmetric β-aminohydroxylation of the olefin or unsaturated substrate and the second step is an oxidation of the deprotected product of the first step to form a D- or L-α-amino acid or a D- or L-α-amino aldehyde.

BACKGROUND

D- and L-α-amino acids are key building blocks for peptides, proteins, pharmaceuticals, and other important biomolecules. Naturally occurring L-α-amino acids are readily available from biological sources. However, enantiomerically pure D-α-amino acids and unnatural L-α-amino acids are more difficult to obtain. Due to their chirality, these compounds can be difficult to synthesize in an enantiomerically pure form. Several compounds within this class have significant economic value. Similarly, and D- and L-α-amino aldehydes are a re-occurring motif in biologically and pharmaceutically important molecules but are difficult to obtain in enantiomerically pure form.

Over the past 20 years, separate and distinct synthetic methodologies have been developed by Sharpless et al. for the vicinal hydroxyamination of olefins. There are three major groups of oxyamination procedures which produce aminoalcohols (Sharpless et al. *J. Am. Chem. Soc.* 1975, 97, 2305; Sharpless et al. *J. Org. Chem.* 1978, 43, 2628; Sharpless et al. *J. Org. Chem.* 1980, 45, 2257), hydroxysulfonamides (Sharpless et al. *J. Org. Chem.* 1976, 41, 177; Sharpless et al. *J. Org. Chem.* 1978, 43, 2544; Sharpless et al. *J. Org. Chem.* 1979, 44, 1953; Sharpless et al. *Org. Syn.* 1980, 61, 85) or hydroxycarbamates (Sharpless et al. *J. Am. Chem. Soc.* 1978, 100, 3596; Sharpless et al. *J. Org. Chem.* 1980, 45, 2710; Sharpless et al. U.S. Pat. Nos. 4,871,855; 4,965,364; 5,126,494; EP 0 395 729). Each oxyamination procedure has unique reaction conditions and includes variations in solvents, auxiliary salts, nucleophiles, temperature, stoichiometric v. catalytic amounts of osmium species and stoichiometric v. catalytic amounts of ligand. Each procedure is highly dependant on the nature of the substrate and possesses unique properties which afford different yields, chemoselectivities, stereoselectivities, regioselectivities and enantioselectivitive outcomes.

1. Aminoalcohols

The first reported oxyamination procedure (Sharpless et al. *J. Am. Chem. Soc.* 1975, 97, 2305) generated aminoalcohols from mono and di substituted olefins, using stoichiometric quantities of a tri-oxo(tert-butylimido)osmium species. The procedure required reductive cleavage of the osmate ester which was performed with lithium aluminum hydride and afforded tertiary vicinal aminoalcohols. Yields were good to excellent, but in some cases, the side product vicinal diol was formed as an undesired by-product. The stereochemistry of addition, in methylene chloride or pyridine, was exclusively cis (Sharpless et al. *J. Org. Chem.* 1978, 43, 2628). In addition, the carbon-nitrogen bond formed was, in every case, at the least substituted olefinic carbon atom. Di and tri-substituted olefins reacted much slower with the generated imido reagent than with monosubstituted alkenes; tetrasubstituted alkenes yielded only the corresponding diol. However, by using a coordinating solvent such as pyridine, higher yields and higher ratios of aminoalcohol to diol were reported. Sharpless et al. *J. Org. Chem.* 1980, 45, 2257; Sharpless et al. *J. Org. Chem.* 1976, 41, 177; Sharpless et al. *J. Org. Chem.* 1978, 43, 2544.

2. Hydroxysulfonamides

Sharpless et al. first demonstrated that hydroxysulfonamides could be obtained using either stoichiometric or catalytic amounts of 1% osmium tetraoxide in the presence of 1.5–5 equivalents of Chloramine-T trihydrate ($TsSO_2NClNa.3H_2O$, Ts=tosylate; commercially obtained) to effect cis addition of a hydroxyl (OH) and an arylsulfonamide moiety (Ar—$SO_2NH$) across a mono or disubstituted olefinic linkages (Sharpless et. al. *J. Org. Chemistry* 1976, 41, 177).

Two procedures were developed to effect hydroxyamination of olefins using sulfonamides. (Sharpless et al. *Org. Syn.* 1980, 61, 85). The first procedure used phase transfer catalysis conditions at 55–60° C. with 1% $OSO_4$, 1:1 v/v, 0.20 Molar $CHCl_3/H_2O$, and benzyltriethylammonium chloride as the phase transfer catalyst. The chloramine T-trihydrate ($TsSO_2NClNa.3H_2O$) was either added directly or formed in situ in water; this solution was then directly used in the phase transfer mixture. The in situ procedure, for generating the chloramine salts, involved stirring a suspension of the arylsulfonamide with an equivalent of sodium hypochlorite (Clorox) until a homogenous solution was obtained. The yields were comparable with those obtained with isolated chloramine salts and the procedure was found most effective for monosubstituted and 1,2 disubstituted olefins. The phase transfer method, however, gave poor results with trisubstituted and 1,1-disubstituted olefins and the procedure did not succeed with diethyl fumarate and 2-cyclohexen-1-one. Sharpless et al. *J. Org. Chem.* 1978, 43, 2544.

A second procedure was carried out in tert-butyl alcohol at 55–60° C. with 1% $OSO_4$, silver nitrate (with or without) and commercially obtained chloramine T-trihydrate ($TsSO_2NClNa.3H_2O$) which provided the only source of water. The procedure did not succeed with tetramethylethylene and cholesterol, and negative results were found with most hindered tri- and tetrasubstituted olefins. Sharpless et. al. *J. Org. Chemistry* 1976, 41, 177; Sharpless et al. *Org. Syn.* 1980, 61, 85. The addition of divalent metal salts such as $AgNO_3$ and $Hg(NO_3)_2$ improved some reactions, however, other reactions suffered deleterious effects from the addition of the metal salts. Sharpless et al. *J. Org Chem.* 1978, 43, 2544; Sharpless et. al. *J. Org. Chemistry* 1976, 41, 177.

Further elaboration on either procedure showed that other sulfonamide derivatives ($ArSO_2NClNa$) could be successfully employed in addition to chioramine T, where Ar=phenyl, o-tolyl, p-chlorophenyl, p-nitrophenyl, and o-carboalkoxyphenyl. Sharpless et al. *J. Org. Chem.* 1978, 43, 2546.

Neither the phase transfer catalyst or tert-butyl alcohol procedures succeeded with tetramethyl ethylene, 2,3-dimethyl-2-octene, diethyl fumarate, or 2-cyclohexen-1-one. Negative results were also obtained with most hindered tri- and tetrasubstituted olefins. Herranz E., MIT Ph.D. Thesis, 1979, 33.

Solvent conditions for the synthesis of the hydroxysulfonamides included organic solvents such as acetonitrile, tert-butyl alcohol, isopropyl alcohol and chloroform which was in contact with the aqueous phase in the phase transfer catalyst procedure.

The tert-butyl alcohol procedure (including other solvents used) was not run with added water; the phase transfer catalyst (PTC) procedure required a biphasic mixture of 1:1 v/v chloroform/water. Recently, however, an improvement was reported which used a 1:1 ratio of organic solvent to water in a homogeneous, rather than a biphasic solution or organic solvent with small amounts of water. These conditions were found to provide optimum enantioselectivity, regioselectivity and improved yields from either the previously described t-butyl alcohol or PTC conditions. Sharpless et al. *Angew. Chemie Intl Ed.* 1996, 35, 451.

The use of chiral ligands with sulfonamides provides enantioselectivity and has been observed to both accelerate and decelerate the rate of catalysis. The hydroxysulfonamide process is a stereoselective cis process. The presence of ligands also has a dramatic effect on the regioselectivity. In a study with no ligand present with methyl cinnamate, the two regioisomers were present in a 2:1 ratio. With the addition of ligand, the ratio was improved to 5:1 or greater. Another positive effect of the ligand was its ability to suppress formation of diol by-product. *Angew. Chemie Intl Ed.* 1996, 35, 451.

Preferred ligands for use with sulfonamides have included the use of monovalent cinchona alkaloids or the bivalent phthalazine based, commercially available $(DHQ)_2PHAL$ and $(DHQD)_2PHAL$ alkaloids. Sharpless et al. *Angew. Chemie Intl Ed.* 1996, 35, 451.

Temperature conditions for the hydroxysulfonamide asymmetric aminohydroxylations have varied from 60° C. to 25° C. for reactions including sulfonamides, auxiliary salts, ligands, phase transfer catalysts and stoichiometric or catalytic osmium species, primarily in organic solvents with small amounts of water. Recently, it has been shown that temperature can be lowered to 0° C. while running the reaction, to obtain product by filtration; many hydroxysulfonamides tend to be highly crystalline. Sharpless et al. *Acta Chemica Scandinavica* 1996 in press.

Cleavage of the sulfonamides, to free aminoalcohols, have been accomplished via standard deprotection conditions including dissolving metals (Na, $NH_3$; Sharpless et al *J. Org. Chem* 1976, 41, 177) and HBr, acetic acid and phenol (Fukuyama et al. *Tetrahedron Lett.* in press).

3. Hydroxycarbamates

A drawback with the hydroxysulfonamide procedure was that cleavage conditions were too strong for some substrates. The use of carbamates to protect the nitrogen, however, provided a methodology which avoided the use of harsh acids or reducing deprotection problems found with hydroxysulfonamides (Sharpless et al. *J. Am. Chem. Soc.* 1978, 100, 3596; Sharpless et al. *J. Org. Chem.* 1980, 45, 2710; Sharpless et al. *Org. Syn.* 1981, 61, 93; Sharpless et al. U.S. Pat. Nos. 4,871,855; 4,965,364; 5,126,494; EP 0 395 729).

Sharpless first demonstrated the synthesis of hydroxycarbamates with the use of N-chloro-N-argentocarbamates (Sharpless et al *J. Am. Chem. Soc.* 1978 100, 3596). The N-chloro-N-argentocarbamates were generated in situ via the addition of N-chlorosodiocarbamates and silver nitrate to a solution of the olefin in acetonitrile or tert-butanol with trace amounts of water (4.5 molar equivalents based on olefin) and 1% of osmium tetroxide catalyst to generate vicinal hydroxycarbamates in generally good yields. The methodology was reported to be more effective with electron deficient olefins such as dimethyl fumarate and trisubstituted olefins were reported to be less readily oxyaminated with N-chloro-N-argentocarbamates than with the chloramine-T procedures (Sharpless et. al. *J. Org. Chem.* 1976, 41, 177).

Sodio-N-chlorocarbamates were always first converted to either argento or mercurio salt analogs. The addition of the $AgNO_3$ or $Hg(NO_3)_2$ salts, to make N-chloro-N-argentocarbamates or mercurio salt analogs, was crucial for the reaction to retain its desired properties. (Sharpless et al *J. Org. Chem.*, 1980, 45, 2711). This was in contrast to the sulfonamide conditions, where the sodio-N-chlorosulfonamide salts could be used directly with either the t-butanol or chloroform/water—phase transfer catalyst procedures (Sharpless et al. *J. Org. Chem.* 1978, 43, 2544).

The addition of nucleophiles such as tetraethylammonium acetate were also proven to be beneficial to the reaction in the procedures using the silver and mercury salts of the chloramines from carbonates. Alternatively, the reactivity and yields were enhanced by addition of excess $AgNO_3$ and $Hg(NO_3)_2$ (over that needed to react with the NaClNCOOR salt) Sharpless et al. *J. Org Chem.* 1980, 45, 2710.

Preferred conditions included employment of $ROCONClNa+Hg(NO_3)_2+Et_4NOAc$ with N-chloro-N-sodiocarbamates; these conditions were recommended as the best procedure for mono, di and tri substituted olefins even including some olefins unreactive in all of the various chloramine T based processes. (Sharpless et al. *Org. Syn.* 1981, 61, 93).

Among the carbamates tried, it was found that both benzyl N-chloro-N-argentocarbamate and tert-butyl N-chloro-N-argentocarbamates (or mercurio analogs) were among the most effective oxidants, especially with addition of nucleophiles such as tetraethylammonium acetate. Other carbamates such as isopropyl, ethyl, menthyl and bornyl derivatives were also used, however, chemo, regio and stereoselectivities were lower. Virtually no asymmetric induction was observed when chiral menthyl or bornyl derived carbamates were employed for hydroxyaminations. (Sharpless et al *J. Am. Chem. Soc.* 1978, 100, 3596).

Sharpless disclosed the use of stoiciometric amounts of a first generation monovalent alkaloid ligand with a tert-butyl derived N-chloro-N-argentocarbamate for hydroxyamination in a series of patent applications directed to ligand accelerated catalytic asymmetric dihydroxylation. These disclosures illustrated an hydroxyamination on trans-stilbene with the use of 1.0 equivalent (stoichiometric to olefin) of monovalent DHQD-p-chlorobenzoate (DHQD= hydroquinidine) ligand, 1 mol % osmium tetroxide, silver nitrate (figure) or mercuric chloride (0.80 equivalents; in protocal), 0.09 Molar acetonitrile (93.11 volume % acetonitrile)/water mix (6.89 volume % water) and tertbutyl derived N-chloro-N-argentocarbamate (1.45 equivalents) at 20° C. (figure) or 60° C. (protocal) for 1 hour. The disclosure reported a 51% ee with a 93% yield of aminoalcohol. (Sharpless et al. U.S. Pat. Nos. 4,871,855; 4,965,364; 5,126, 494; EP 0 395 729).

In a review on ligand accelerated catalysis, Sharpless et al. noted that a 92% ee had been achieved in a stoichiometric reaction of trioxo-(tert-butylimido) osmium with stilbene in the presence of DHQD-CLB at ambient temperatures (Sharpless et al. *Angew. Chem. Int. Ed. Engl.* 1995, 34, 1059, ref. 80 "unpublished results"); this mention did not disclose reaction conditions.

Recently, an oxyamination reaction for the hemisynthesis of taxol and analogs was reported using a tertbutyl derived N-chloro-N-argentocarba-mate, excess silver nitrate or other metallic salts, with the use of either catalytic or stoichiometric amounts of osmium and the addition of stoichiometric amounts of monovalent DHQD (hydroquinidine), DHQ (hydroquinine) ligands in an unsuccessful attempt to influence the diastereoselectivity and the regioselectivity of the aminohydroxylation process. Solvent conditions varied from acetonitrile, toluene or pyridine, and the reactions were carried out at 4° C. to room temperature, in the dark. The study reported that quinuclidine ligands had no effect on the amino alcohol yields but found that the addition of chiral tertiary amines had some beneficial effect on the yields of the various amino alcohol isomers formed. (Mangatal et al. *Tetrahedron* 1989 45, 4177). However, the two pseudoenantiomeric alkaloid ligands (i.e. DHQ-OAc and DHQD-OAc; OAc=acetate) gave a mixture of stereo and regioisomeric products. The result indicates that this particular hydroxyamination process (be it stoichiometric or catalytic was unclear) had exhibited no "asymmetric" effects. The procedure can therefore not be regarded as an asymmetric aminohydroxylation.

As a whole, the prior art uses hydroxycarbamates which always run at room temperature with either argento or mercurio salt analogs, monovalent ligands, stoichiometric or catalytic osmium species and organic solvents with trace amounts of water. (Sharpless et al. *J. Am. Chem. Soc.* 1978, 100, 3596; Sharpless et al. *J. Org. Chem.* 1980, 45, 2710; Sharpless et al. U.S. Pat. Nos. 4,871,855; 4,965,364; 5,126,494; EP 0 395 729).

Cleavages of the hydroxycarbamates, to free aminoalcohols, are well known in the art and include mild acid or base hydrolysis and catalytic hydrogenolysis, depending on the attached functionality to the carbamate. (Greene, *Protective Groups in Organic Synthesis,* 1981, Wiley, 1st edn. pp. 223–249).

What is needed is an improved method for synthesizing D- and L-α-amino acids and D- and L-α-amino aldehydes using olefins as starting materials.

SUMMARY OF THE INVENTION

One aspect of the invention is directed to methods for the conversion of olefinic substrates to form asymmetric α-amino acid products. The method employs two steps.

In the first step the olefinic substrate is catalytically converted by means of an addition reaction to form a protected asymmetric β-aminohydroxide product having a protected amino radical and a hydroxyl radical. The conversion employs a reaction solution which includes a source of the protected amino radical, osmium as a catalyst, a chiral ligand for enantiomerically directing the asymmetric addition, and a solvent.

There are several modes for accomplishing this first step. In a first preferred mode, the source of the protected amino radical is a carbamate. In a second preferred mode, the source of the protected amino radical is a sulfonamide. In the first preferred mode, the chiral ligand may be present and soluble within the reaction solution at a concentration within a range approximately excellent to the catalytic concentration of the osmnium. The solvent may have an organic component within which the olefinic substrate and carbamate are present and soluble at stoichiometric concentrations and within which the osmium is present and soluble in catalytic concentrations. The solvent may also include an aqueous component present at 10% or greater on a volume basis. Alternatively, the chiral ligand may be present and soluble within the reaction solution at a molar concentration which is approximately equivalent to the catalytic concentration of the osmium but which is less than the stoichiometric concentration of the olefinic substrate and carbamate.

In the second step, the hydroxyl radical on the asymmetric β-aminohydroxide product of the first step is oxidized to form the asymmetric α-amino acid product. The protected amino radical may be deprotected either prior to or after the oxidation of the hydroxyl radical.

Another aspect of the invention is directed to methods for the conversion of olefinic substrates to form asymmetric α-amino aldehyde products. This second aspect of the invention employs two steps, viz.

1. An addition reaction wherein the olefinic substrate is converted to the protected asymmetric β-aminohydroxide product described above; and 2. An oxidation step where the product of the first step is converted to an asymmetric α-amino aldehyde product.

The protected amino radical may be deprotected either before or after the oxidation step. In a preferred mode, the deprotection is perform simultaneously with the oxidation step.

SYNTHETIC PROTOCALS

General Experimental

Figure 1:
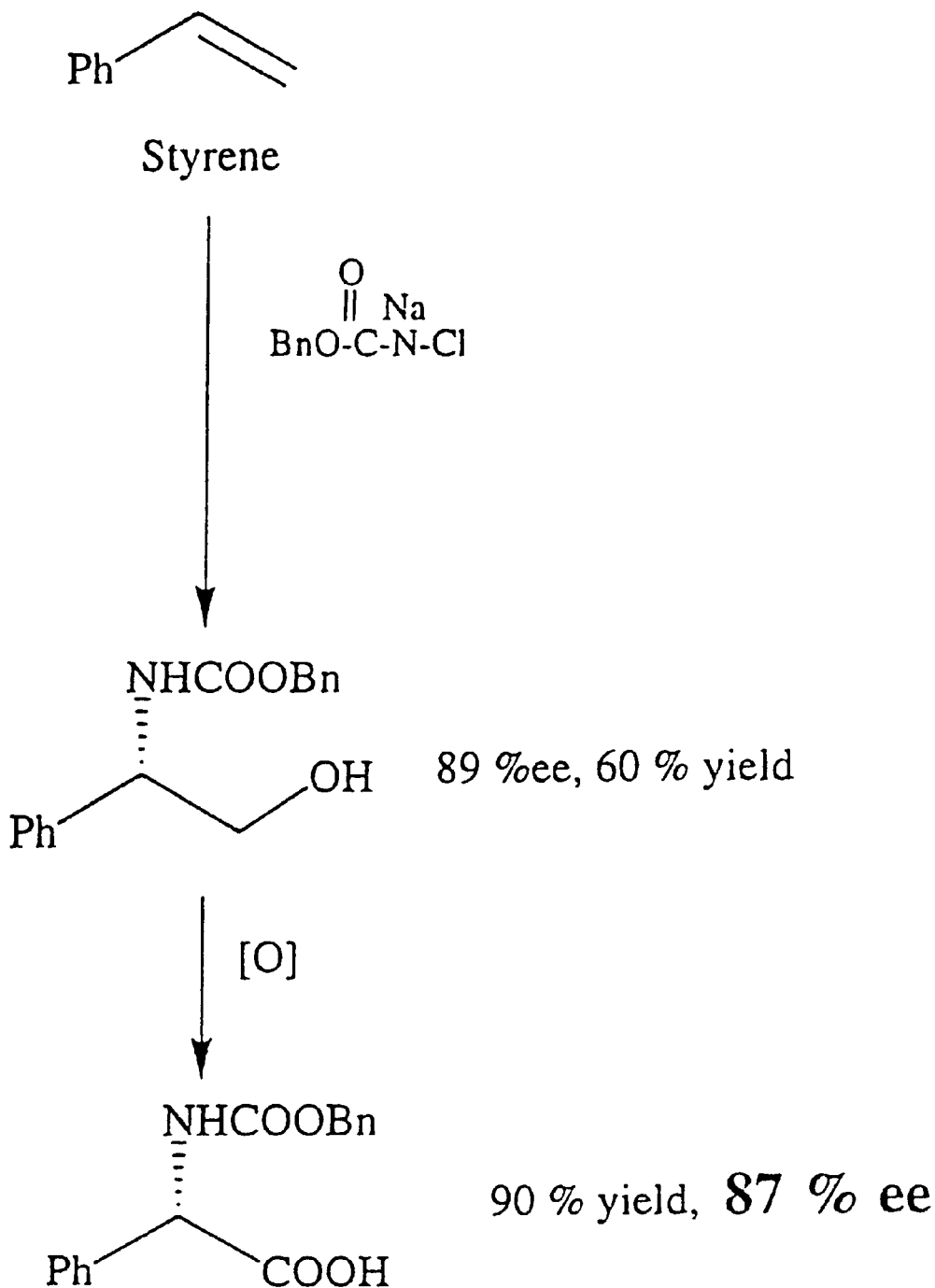
FIG. 1 illustrates the asymmetric aminohydroxylation of styrene to its corresponding α-hydroxy-β-benzylcarbamate. The α-hydroxy-β-benzylcarbamate is subsequently oxidized to the amino acid. Oxidation conditions include, but are not limited to: $RuCl_3$, $H_5IO6$ oxidation to free acid: Sharpless et al *J. Org. Chem.* 3937 (46), 1981; $KMnO_4$/NaOH: Garner et al., Tetrahedron Lett., 5855–58, 1984; $RuO_2$: Martin, Tetrahedron Lett., 2701–02, 1988. $K_2CrO7/H_2SO_4$:J. Am Chem. Soc., 2498, 1960; PtO2: *J. Org. Chem.* 4898, 1987.

All reagents and solvents were purchased from commercial sources and used as received unless stated otherwise. All commercial chemicals were used without purification and their stoichiometries were calculated based on the reported purities from the manufacturer. $(DHQD)_2PHAL, 95\%$ (hydroquinidine 1,4-phthalazinediyl diether), $(DHQ)_2PHAL$, 97% (hydroquinine 1,4-phthalazinediyl diether), chloramine-T-hydrate 98% (N-chloro-p-toluenesulfonamide, sodium salt) are commercially available from Aldrich Chemical Company. Additionally, the $(DHQ)_2$ and $(DHQD)_2$ ligands can be prepared from the procedure of Sharpless et al. *J. Org. Chem.* 1992, 57, 2768. Melting points were measured without correction with a Thomas-Hoover capillary apparatus. Optical rotations were recorded on an Autopol III polarimeter (Rudolph Research, Fairfield, N.J.). $^1H$ and $^{13}C$ NMR spectra were recorded on a Bruker AMX 400 instrument. Stoichiometries are calculated based on the purities reported by the manufacturer (trans-stilbene: 96%; Chloramine-T trihydrate: 98%). The $K_2OsO_2(OH)_4$ should be mauve rather than brown/black and should be dry for the best yields and ee's (the hygroscopic nature of the salt affects the amount of osmium dispensed). All new compounds gave satisfactory spectroscopic analyses ($^1H$-NMR, IR, HRMS). Enantiomeric excesses (ee's) were determined by HPLC using Chiracel columns (Daicel Chemical Industries) and isopropanol/hexane (v/v) mobile phases; the retention time of the major enantiomer from the $(DHQ)_2$-PHAL reaction is in italics. The vicinal hydroxysulfonamides derived from AA reactions using $(DHQ)_2$-PHAL as the chiral ligand were correlated to compounds of known absolute configuration by HPLC.

Oxidation Conditions to Aminoacids from Hydroxycarbamates or Hydroxysulfonamides Procedure as adapted from Sharpless et al *J. Org. Chem.* 3937 (46), 1981. A convenient vial or flask is charged with a magnetic stirring bar, 2 mL of carbon tetracloride, 2 mL of acetonitrile, 3 mL of water, 1 mmol of β-sulfonamide alcohol or β-carbamate alcohol substrate, and 4.1 mmol of (4.1 equiv.) of periodic acid, and 5 mg (2.2 mol %) of ruthenium trichloride hydrate (all reagents commercially available from Aldrich). The reaction mixture is stirred at room temperature for 0.5 to 1 h. Then 10 mL of ethylacetate (EtOAc) is added and the phases are separated. The aqueous phase is extracted 3 times with EtOAc. The combined organic phases are then dried(MgSO4), filtered through Celite pad. 0.90 mmol of NMR pure product was obtained after concentration and vacuum drying. The acid is then transferred its methyl ester and reduced back to (S) N-benzyl phenylglycinol. Chirality is maintained.

Other oxidation conditions include, but are not limited to: $KMnO_4$/NaOH: Garner et al., Tetrahedron Lett., 5855–58, 1984; $RuO_2$: Martin, Tetrahedron Lett., 2701–02, 1988. $K_2CrO7/H_2SO_4$: J. Am Chem. Soc., 2498, 1960; PtO2: *J. Org. Chem.* 4898, 1987.

Oxidation Conditions to Aminoaldehydes from Hydroxycarbamates or Hydroxysulfonamides Procedure adapted from Russo, et al *J. Org. Chem.* 3589 (58), 1993. A solution of β-sulfonamide alcohol or β-carbamate alcohol substrate (10.7 mmol) in 15 mL of $CH_2Cl_2$ was cooled to 0° C. The rapidly stirring solution was treated with 6.9 mL in $CH_2Cl_2$ of TEMPO (Aldrich), 1.5 mLof 0.75 M KBr, and 0.22 g of Aliquat 336. Aqueous NaOCl (0.4 M, 67 mL) was brought to pH 9 with $NaHCO_3$ and added dropwise. After the addition of the aqueous NaOCl solution, the biphasic reaction was stirred for an additional 10 min. at room temperature. The pH of the mixture was adjusted to 12 with NaOH when the reaction was complete.

Other oxidation conditions include, but are not limited to oxidations well known in the art, including Swern, $SO_3$/pyridine or PCC oxidations, to achieve the aldehyde.

Chloramine Sodium Salt Preparation

Procedure as adapted from Campbell et al. *Chem. Rev.*, 1978, 78, 65.

General Asymmetric Aminohydroxylation Conditions with Carbamates

To a solution of NaOH (3.05 equivalents) in 0.13 Molar equivalent of water to olefin is added desired carbamate (3.10 equivalents). The resulting solution is stirred at room temperature for 10 min and then t-butyl hypochlorite (3.05 equivalents; Aldrich Chemical) is added dropwise. The above solution is stirred for another 10 min and then 0.13 Molar equivalent of n-propanol (t-butanol or acetonitrile can be substituted) and $(DHQ)_2$-PHAL (0.05 equivalents, 5 mol %; $DHQD_2$-PHAL obtains antipode) are added to form a homogeneous solution. The reaction mixture is immersed in a room temperature bath and added substrate olefin (1 equivalents) and $K_2OsO_2(OH)_4$ (0.04 equivalents, 4 mol %) are then added. The reaction is stirred for 45 min with the color changing from light green to light yellow, followed by quenching by addition of aqueous sodium sulfite; the phases are separated, and the aqueous phase was extracted with ethyl acetate. The combined organic extracts are washed with water and brine, dried over $MgSO_4$ and the solvent concentrated to give the crude product. Flash chromatography of this material provides the hydroxycarbamate product.

Solvent Variations

Preferred solvents include acetonitrile, n-propanol, tert-butanol.

Suitable solvents include methanol, ethanol, n-butanol, n-pentanol, 2-Propanol, 2-Butanol, tert-butanol, ethylene glycol; nitrites: acetonitrile, propionitrile; ethers: tetrahydrofurane, diethyl ether, tert. butyl methyl ether, dimethoxyethane, 1,4-dioxane; miscellaneous: dimethyl formamide, acetone benzene, toluene, chloroform, methylene chloride.

Percent water/Organic Solvent Variations

Two key points are that the ee and especially the yields are lower in the low water range (see FIGS. 11 and 12). No reaction is seen with only 2 to 4 equiv of water present which must be much less than 0.1% water These same "minuscule" amounts of water" conditions work great for the silver and mercury salts of the N-chlorocarbamates in the old catalytic aminohydroylation process with no chiral ligands present.

Solvent Concentration Variations

In its present form the process starts to give lower selectivities for some substrates when the concentration of olefin (which of course prescribes the standard concentration of all the other species) gets much above 0.1 molar.

Ligand Variations

The ligand can range from ca. 1 to 10 mol % (less is appropriate for lower temperatures; eg. 1% might be enough at 0° C. and 10% would probably be needed to keep the % ee at reasonable levels if the temperature reaches 35 or 40° C. In practice, the molarity of the ligand matters and the amount of ligand needed to realize the "ceiling ee" scales directly with the reaction concentration (ie if twice the volume of solvent is used, then the mol % of ligand added must also double to keep its molarity constant and correspondingly if the reaction is run twice as concentrated as usual (see general recipe below) then half of the usual mol % ligand gives the needed ligand molarity). Because the crucial binding of the ligand is an extremely rapid bimolecular process, the equilibrium constant is highly sensitive to temperature which is why the molarity of ligand needed, increases rapidly with temperature.

Osmium Variations

The amount of Os catalyst can range from 0.5% (probably even less in the very best cases, and in any case the number will drop as the process if further improved) to 10 or even 20%. The general procedure conditions uses 4% to have fast reaction times, but 2% is good for most cases. The high loadings of 20%, for example, is needed to achieve reasonable rates with very poor substrates (this conclusion follows from the extensive experience by us and others with the AD, where in desparate situations 20 or more % Os catalyst is needed.

Temperature Variations

For most cases, the carbamate AA process is run between 10 and 25 degrees C. There may be cases where 0 degrees— up to 35 to 40 degrees may be advantageous depending on substrate.

Deprotection Conditions of Carbamate to Free Amine t-BOC: TFA procedure: Lundt et al *Int. J. Pept. Protein Res.*, 1978, 12, 258; HCl procedure: Stahl et al. *J. Org. Chem.*, 1978, 43, 2285.

Benzyl carbamate: Hydrogenation procedure: Bergman et al *Ber.*, 1932, 65, 1192.

Ethyl and methyl carbamate: Trimethylsilyliodide procedure: Lott et al. *J. Chem. Soc. Chem. Comm* 1979, 495; HBr procedure: Wani et al *J. Am. Chem. Soc.*, 1972 94, 3631.

Transformation of R-COOH to R-COOMe

Procedure as adapted from Chan et al. *Synthesis* 1983, 201.

Syntheses of a Representative Set of Hydroxycarbamates

Synthesis of Compound 1

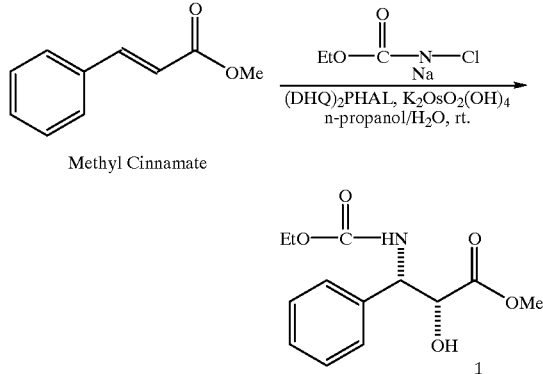

Methyl Cinnamate

1

To a solution of NaOH (0.112 g, 3.05 mmol) in 7.5 mL of water was added ethyl carbamate (0.276 g, 3.10 mmol). The resulting solution was stirred at room temperature for 10 min and then t-butyl hypochlorite (0.331 g, 3.05 mmol; Aldrich Chemical) was added dropwise. The above solution was stirred for another 10 min and then 7.5 mL of n-propanol and (DHQ)$_2$-PHAL (40 mg, 0.05 mmol, 5 mol %) were added to form a homogeneous solution. The reaction mixture was immersed in a room temperature bath and added methyl cinnamate (0.162 g, 1 mmol) and K$_2$OsO$_2$(OH)$_4$ (14.7 mg, 0.04 mmol, 4 mol %) were then added. The reaction was stirred for 45 min with the color changing from light green to light yellow, followed by quenching by addition of aqueous sodium sulfite (sat. 6 mL); the phases were separated, and the aqueous phase was extracted with ethyl acetate (3×5 mL). The combined organic extracts were washed with water and brine, dried over MgSO$_4$ and the solvent concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided 0.21 g (78% yield, >99% ee) of (2R,3S) vicinal hydroxycarbamate product.

If benzyl carbamate was used, 4 mL of n-propanol was added with water to dissolve all of benzyl carbamate before adding t-butyl hypochlorite.

Synthesis of Compound 2

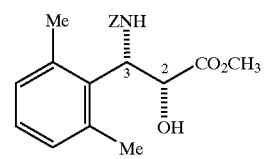

2

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then 2',6'-dimethyl cinnamate (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 3

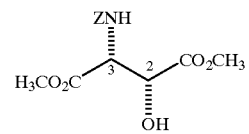

3

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13

Molar; based on initial olefin concentration) and (DHQ)$_2$-PHAL (5 mol %) were added to form a homogeneous solution. The reaction mixture was immersed in a room temperature bath and then dimethylfumarate (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 4

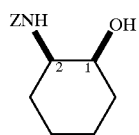

4

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then cyclohexene (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 5

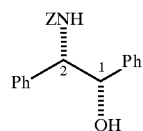

5

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then trans-stilbene (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. This is an example of a solution-to-solid and solid-to-solid entry—the work-up required simple filtration which provided the vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 6

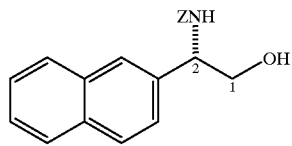

6

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then 2-vinylnaphthalene (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. This is an example of a solution-to-solid and solid-to-solid entry —the work-up required simple filtration which provided the vicinal hydroxycarbamate products.

If benzyl carbamate was used, an additional 0.25 M volume of n-propanol was added with water to dissolve all of benzyl carbamate before adding t-butyl hypochlorite.

Synthesis of Compound 7

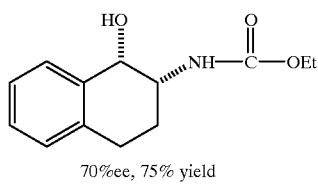

70%ee, 75% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then 1,2-dihydronaphthalene (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 8

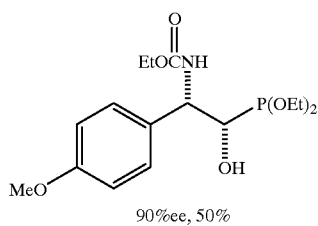

90%ee, 50%

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then trans-diethyl p-methoxy styryl phosphonate (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 9

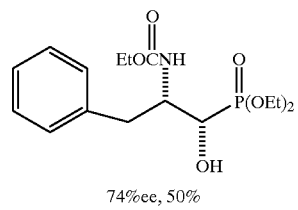

74%ee, 50%

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution, The reaction mixture was immersed in a room temperature bath and then trans-diethyl 3-phenyl propenyl phosphonate (1 equivalent; Aldrich) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 10

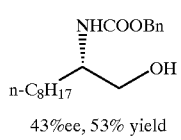

43%ee, 53% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and $(DHQ)_2$-PHAL (5 mol %) were added to form a homogeneous solution. The reaction mixture was immersed in a room temperature bath and then 1-decene (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate. Flash chromatography (6:4:1 hexane/$CHCl_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 11

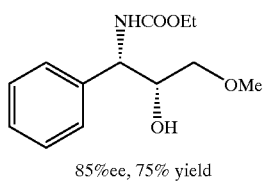

85%ee, 75% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and $(DHQ)_2$-PHAL (5 mol %) were added to form a homogeneous solution. The reaction mixture was immersed in a room temperature bath and then cinnamyl alcohol methyl ether (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate. Flash chromatography (6:4:1 hexane/$CHCl_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 12

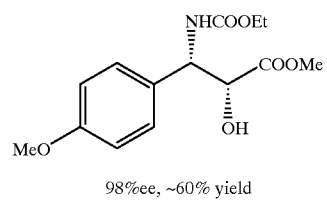

98%ee, ~60% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and $(DHQ)_2$-PHAL (5 mol %) were added to form a homogeneous solution. The reaction mixture was immersed in a room temperature bath and then methyl trans 4-methoxycinnamate (1 equivalent; Aldrich) and $K_2OsO_2(OH)_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over $MgSO_4$ and the solvent was concentrated to give the crude product, which also contained the ethyl carbamate by-product produced upon the reduction of the excess N-chlora-N-sodiocarbamate. Flash chromatography (6:4:1 hexane/$CHCl_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 13

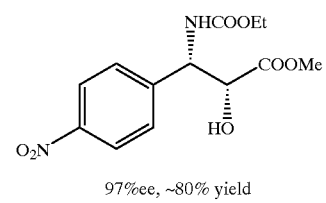

97%ee, ~80% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then methyl-trans-4-nitrocinnamate (1 equivalent) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of Compound 14

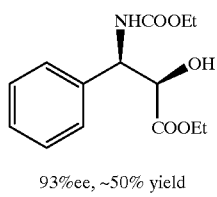

93%ee, ~50% yield

To a solution of NaOH (3.05 equivalents) in water (0.13 Molar; based on initial olefin concentration) was added ethyl carbamate (3.10 equivalents). The resulting solution was stirred at room temperature for 10 minutes and then t-butyl hypochlorite (3.05 equivalents; Aldrich Chemical Company) was added dropwise at 0° C. The above solution was stirred for another 10 minutes and then n-propanol (0.13 Molar; based on initial olefin concentration) and (DHQ)$_2$-PHAL (5 mol %) were added to form a homogeneous solution. The reaction mixture was immersed in a room temperature bath and then ethyl cis cinnamate (1 equivalent) and K$_2$OsO$_2$(OH)$_4$ (4 mol %) were then added. The reaction was stirred for 45 minutes at room temperature with the color changing from light green to light yellow, followed by quenching by addition of aqueous sodium sulfite (saturated 0.17 Molar; based on initial olefin concentration). The phases were separated, and the aqueous phase was extracted with ethyl acetate (3×0.20 M volumes). The combined organic extracts were washed with water and brine, dried over MgSO$_4$ and the solvent was concentrated to give the crude product, which also contained the ethyl carbamate by-product produced upon the reduction of the excess N-chlora-N-sodiocarbamate. Flash chromatography (6:4:1 hexane/CHCl$_3$/MeOH) of this material provided vicinal hydroxycarbamate product.

If benzyl carbamate was used, an additional 0.25 M volume of n-propanol was added with water to dissolve all of benzyl carbamate before adding t-butyl hypochlorite.

Synthesis of (2R,3S)-(+)-Methyl-N-(p-toluenesulfonyl)-2-hydroxy-3-amino-3-phenyl-propionate in t-BuOH

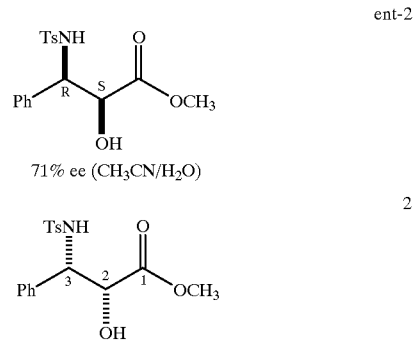

Compound 2.

To a 2 L round-bottom flask, equipped with a mechanical stirrer and a thermometer, was added (DHQ)-PHAL (6.6 g, 2.5 mol %), t-BuOH (600 mL) and H$_2$O (600 mL). The flask was immersed in a room temperature water bath. To the resulting homogeneous solution was added in order 290.4 g (1.01 mol) of Chloramine-T trihydrate (ca. 4/5 of the total added which is in 338 g, 1.18 mol), methyl cinnamate (27.2 g, 167.6 mmol, half of the total amount of olefin, which is 54.4 g, 0.33 mol; Aldrich chemical company) and potassium osmate(VI; Aldrich) (2.5 g, 2.0 mol %). As the reaction was stirred, the color changed from yellow to green in 15 min and then back to yellow after 90 min; TLC(EtOAc/Hexane, v/v=4/6) revealed that the disappearance of olefin coincided with the return of the yellow color. The flask was then immersed in an ice bath (0° C.) for 20 min. (During this cooling, the crystals of precipitated product made their first appearance.) To this cold, stirred suspension the remainder of the Chloramine-T trihydrate (48.4 g, 0.168 mol) and the second portion of methyl cinnamate (13.6 g, 84 mmol) was added. The ice bath was replaced by the room temperature water bath, and the new olefin charge was consumed in about 45 min during which time the color changed as before from yellow to green and back to yellow again. The resulting mixture was cooled back to 0° C. for over 15 min and the third and last portion of methyl cinnamate (13.6 g, 84 mmol) was added. The reaction was returned to the room-temperature water bath and the remaining olefin was consumed in about 45 min with the above noted sequence of color changes. The flask was again immersed in an ice bath (0° C.) for about 20 min. Essentially all of the product precipitated out of solution and was isolated by filtration, washed twice with cold (ca 0° C.) 100 mL portions of t-BuOH/H$_2$O (v/v=1/1) to yield 81.1 g of (2R,3S)-(+)-methyl-N-(p-toluenesulfonyl)-2-hydroxy-3-amino-3-phenyl propionate (2) (69% yield, 82% ee, m.p. 147–148° C.; for racemic: m.p. 125–126° C. 4c).

A 6.3 g portion of this crude 2 was triturated with EtOAc at room temperature (1×75 mL, 1×35 mL and 2×20 mL), the solid triturand of 2 remaining after these triturations is of low ee and is discarded. Concentration of the combined triturates afforded 5.3 g of enantiomerically enriched 2 (58% yield, 92% ee), three recrystallizations from MeOH gave 3.2 g of enantiomerically pure product 2 (35% yield based on 1), m.p. 154–155° C.; [a]\o(25,D)=+19.8° (c 0.5, 95% EtOH); $^1$H NMR (400 MHz, DMSO/D$_2$O) δ2.23 (s, 3H), 3.45 (s, 3H), 4.17 (d, J=4.0 Hz, 1H), 4.65 (d, J=4.0 Hz, 1H), 7.08–7.19 (m, 8H), 7.40 (d, J=8.2 Hz, 2H); $^{13}$C NMR (100

MHz, DMSO) δ171.8, 141.9, 138.4, 138.7, 128.9, 127.6, 127.3, 126.9, 126.4, 74.4, 60.1, 51.6, 20.9.

Synthesis of (2R,3S)-(+)-Methyl-N-(p-toluenesulfonyl)-2-hydroxy-3-amino-3-phenyl-propionate (2) in n-Propanol:

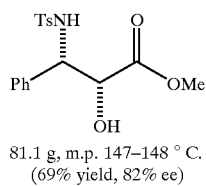

2

81.1 g, m.p. 147–148 °C.
(69% yield, 82% ee)

To a solution of (DHQ)$_2$-PHAL (2.20 g, 2.80 mmol, 5 mol %) in n-Propanol (100 mL) and water (100 ml) in 500 mL Erlenmeyer or round-bottomed flask were added in order, methyl cinnamate (9.08 g, 56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 3 hr. Over the course of the reaction, the color changed from brown to deep green and then back to yellow as hydroxysulfonamide product appeared as white precipitates. The flask was then immersed in an ice bath (0° C.) for 20 min. During this cooling, almost all of crystalline hydroxysulfonamide product precipitated from the reaction solution. The product was isolated by filtration and the crude solid was washed once with cold (ca 5° C.) 1:1 n-Propanol/H$_2$O(15 mL) to yield 11.7 g of (2R,3S)-(+)-methyl-N-(p-toluenesulfonyl)-2-hydroxy-3-amino-3-phenyl propionate (60% yield, 89% ee).

Synthesis of (2R,3S)-2-hydroxy-3-amino-3-phenylpropionic acid (3)

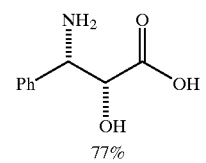

3

77%

Compound 3.

A heavy-walled borosilicate pressure bottle was charged with the enantiomerically enriched (92% ee) 2 [i.e. the triturated but not recrystallized material (vide supra)] (1.25 g, 3.6 mmol), phenol (1.04 g, 11.1 mmol) and excess 33% hydrogen bromide in acetic acid (20 mL, 0.117 mol, Acros). The bottle was sealed with a bushing, having a Teflon-lined cap, before being immersed completely in an oil bath. The bath was maintained at 75° C. for 10–12 h. The resulting solution was then concentrated in vacuo to about 10 mL (water pump followed by an oil pump which was protected by a 0° C. aqueous KOH bubbler). The crude solution was purified by ion-exchange chromatography (Amberlite IR-120 resin, 35 g), elueting with 80 mL of water (to remove impurities), then with 80 mL of 10% ammonium hydroxide (start with a dilute solution due the heat generated in the ion exchange process) followed by 80 mL of 40% ammonium hydroxide. Collection of the ammonium hydroxide eluate gave a solution of the ammonium salt of 3 which upon lyophilization yielded pure (2R,3S)-2-hydroxy-3-amino-3-phenylpropionic acid (37, 0.51 g, 77%). m.p. 235° C., decomp. (literature: Deng et. al J. Org. Chem. 57, (1992), 4320: m.p. 238° C., decomp.); rotation after conversion to the hydrochloride salt is [a]\o(25,D)=–14.5° (c 0.37, MeOH; [a]\o(25,D) –15.1° c 0.365, MeOH). 1H NMR (400 MHz, D$_2$O) δ4.09 (d, J=6.0 Hz, 1H), 4.32 (d, J=6.0 Hz, 1H), 7.21–7.41 (m, 5H); $^{13}$C NMR (100 MHz, D$_2$O/DMSO) d 177.7, 135.4, 130.9, 130.7, 128.9, 75.0, 59.0.

N-Benzoyl-(2R,3S)-2-hydroxy-3-amino-3-phenylpropionic Acid (4)

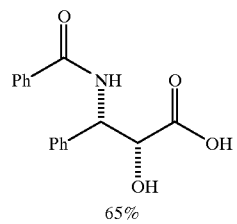

4

65%

Compound 4.

The enantiomerically enriched 37 (0.43 g, 2.37 mmol) was converted to N-benzoyl-(2R,3S)-2-hydroxy-3-amino-3-phenylpropionic acid (4, 0.44 g, 65%) according to our earlier Schotten-Baumann-based procedure for this same transformation (Sharpless et al. J. Org. Chem. 59 (1994), 5104). Chemically and enantiomerically pure 4 was isolated by simple filtration of the solid which appeared when the pH of the reaction mixture was adjusted to ca. 2 by addition of aqueous HCl. m.p. 166–167° C. (lit: Ojima et al. J. Org. Chem 56 (1991) 1681: 167–169° C.); [a]\o(25,D) –34.0° (c 0.50, EtOH) (lit: Sharpless et al. J. Org. Chem. 1976, 41, 177: [a]\o(25,D) –35.9° c 0.565, EtOH); lit3d [a]\o(25,D) –35.5° (c 1.07, EtOH); 1H NMR (400 MHz, DMSQ) δ4.37 (d, J=4.3 Hz, 1H), 5.46 (dd, J=8.8, 4.2 Hz, 1H), 7.22–7.55 (m, 9H), 7.84 (d, J=7.2 Hz, 1H), 8.60 (d, J=8.9 Hz, 1H), 12.73 (br, 1H); $^{13}$C NMR (100 MHz, DMSO) δ173.5, 166.0, 140.3, 134.4, 131.4, 128.4, 128.0, 127.4, 127.2, 126.9, 73.6, 55.8.

General Procedure 1: Catalytic Asymmetric Arninohydroxylation in 1:1 Acetonitrile/Water (Used for Synthesis of Compounds 2, 5, 6, 7, 8 or 9)

Figure 4:
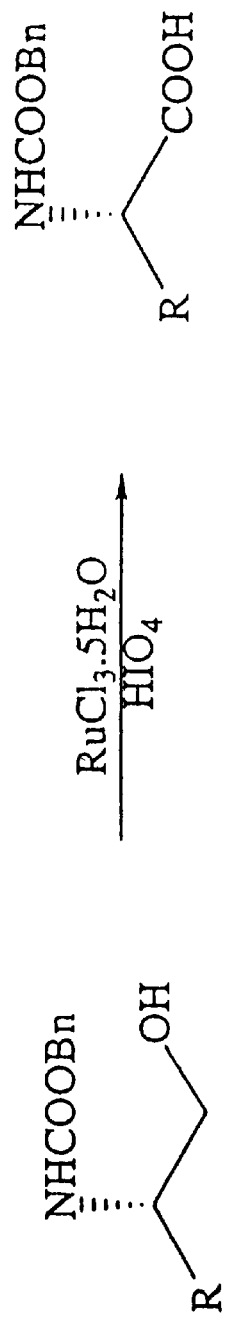
FIG. 4 illustrates oxidation conditions to the protected amino acid from the carbamate (benzyl carbamate is shown, however other carbamates commonly used in the AA procedure are possible) with indicated nonaromatic "R" groups.
Figure 5:
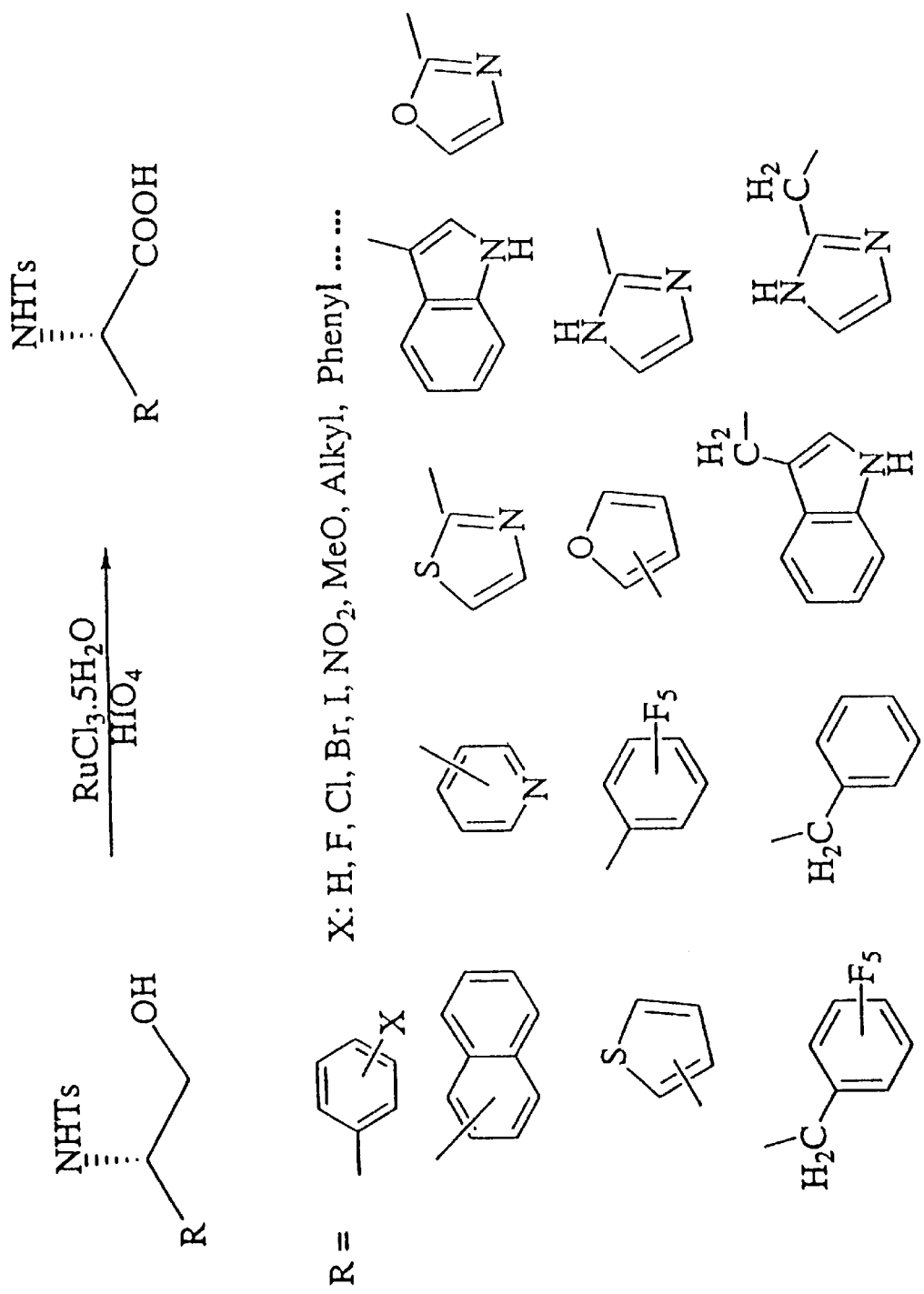
FIG. 5 illustrates oxidation conditions to the protected amino acid from the sulfonamide (tosyl (Ts) sulfonamide is shown, however other sulfonamides commonly used in the AA procedure are possible) with indicated aromatic and heteroaromatic "R" groups.
Figure 6:
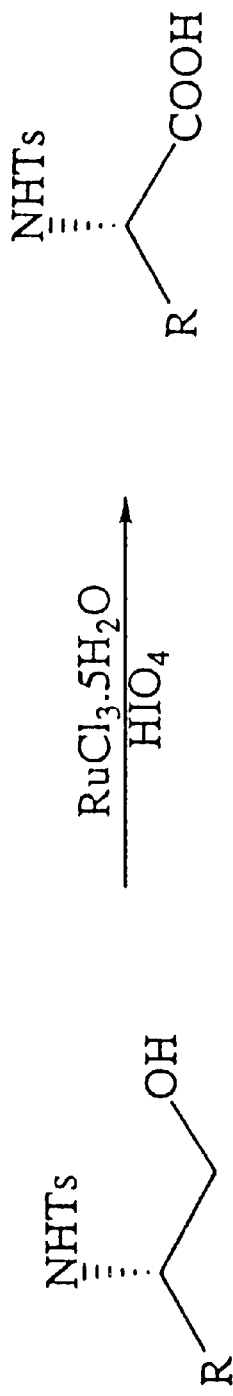
FIG. 6 illustrates oxidation conditions to the protected amino acid from the sulfonamide (tosyl (Ts) sulfonamide is shown, however other sulfonamides commonly used in the AA procedure are possible) with indicated nonaromatic "R" groups.
Figure 7:
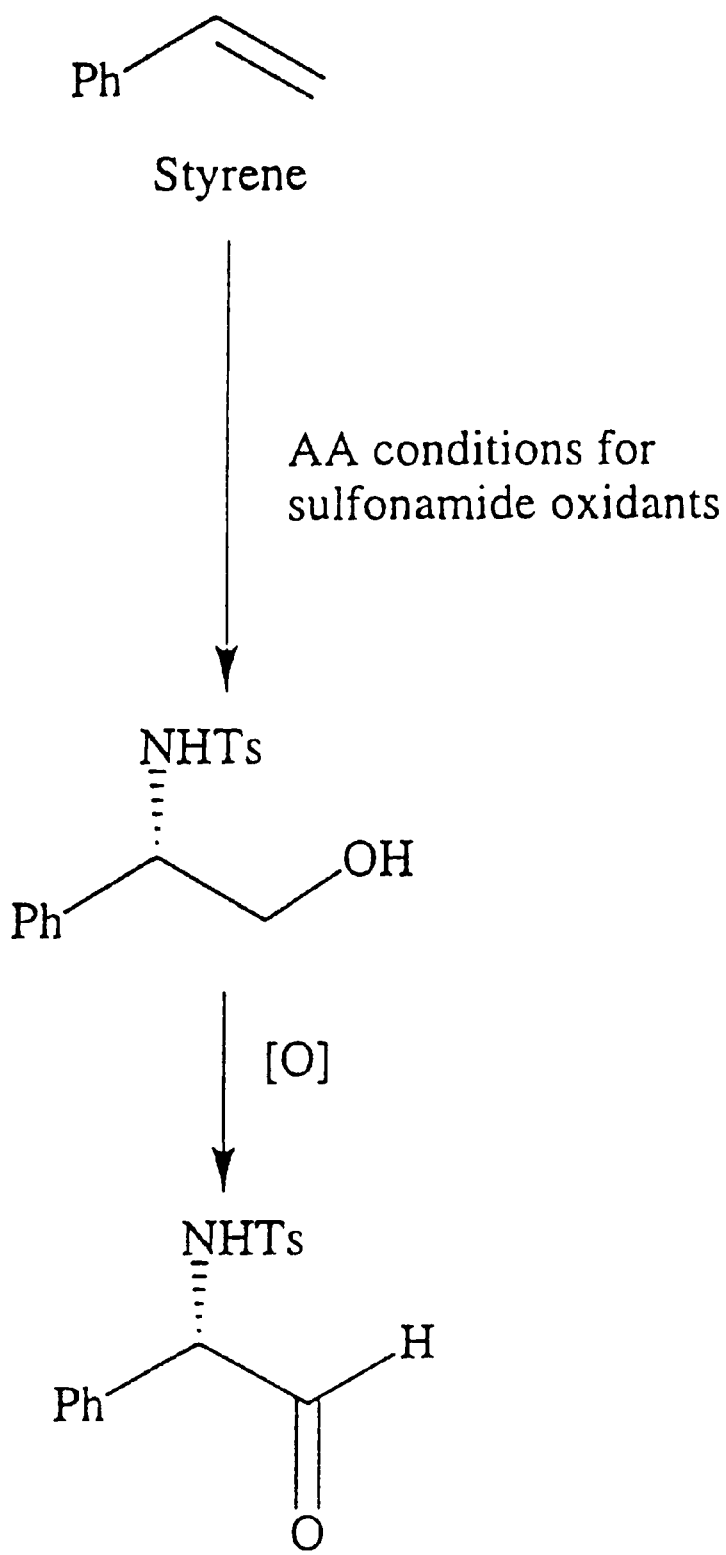
FIG. 7 illustrates the oxidation of the α-hydroxy-β-sulfonamide derived from styrene. Oxidation conditions include, but are not limited to oxidations well known in the art, including TEMPO, Swern, $SO_3$/pyridine or PCC oxidations, to achieve the aldehyde.
Figure 8:
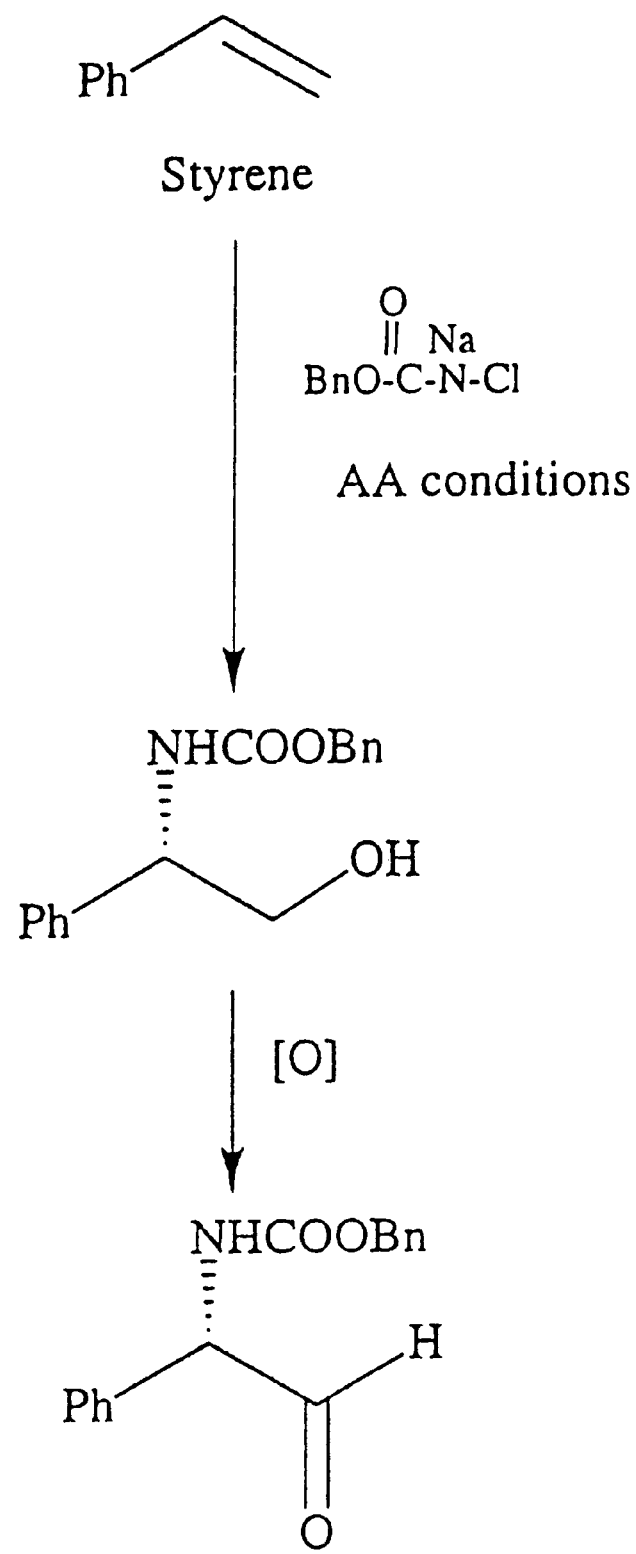
FIG. 8 illustrates the oxidation of the α-hydroxy-β-benzylcarbamate derived from styrene. Oxidation conditions include, but are not limited to oxidations well known in the art, including TEMPO, Swern, $SO_3$/pyridine or PCC oxidations, to achieve the aldehyde.

To a stirred solution of (DHQ)$_2$-PHAL (0.11 g, 0.14 mmol, 5 mol %) in 20 mL of acetonitrile and 20 mL of water, in any convenient-sized glass vessel or vial, was added desired olefin (all commercially available from Aldrich, 2.8 mmol), Chloramine-T trihydrate (2.42 g, 8.4 mmol, 3 eq) and K$_2$OsO$_2$(OH)$_4$ (41.6 mg, 0.112 mmol, 4 mol %). As the reaction proceeded to completion over the course of about one and half hours at room temperature, the color of the solution changed from yellow to pale green, then deep green and finally back to yellow (for entry 3 in Table 1, the yellow color remains throughout). After addition of aqueous sodium sulfite (1.0 g in 15 mL H$_2$O), the phases were separated, and the aqueous phase extracted with ethyl acetate (3×15 mL). The combined organic extracts were washed with brine, dried over MgSO$_4$ and the solvent concentrated to give the crude product, which also contains the p-toluenesulfonamide by-product produced upon the reduction of the excess Chloramine-T. In the case of the ethyl crotonate derivative, product 5, flash chromatography (6:4:1 hexane/CHCl3/MeOH) of this material provided 0.44 g (52% yield, 74% ee) of (2R,3S)-ethyl-N-(p-toluenesulfonyl)-2-hydroxy-3-amino-butanoate (5) as a clear oil eluting before the p-toluenesulfonamide impurity (52% yield, 74% ee). Similar purification provides compounds 2, 6, 7, 8 and 9. with the indicated yields and conditions shown in FIG. 4. NOTE: Replacement of the 3 eq of Chloramine-T with 1.5 eq of Chloramine-T and 1.5 eq of $Et_4NOAc$ gives comparable results and reduces the amount of p-toluenesulfonamide by-product formed. This can greatly simplify product isolation, especially in cases where the product and the toluenesulfonamide have similar chromatographic mobilities.

General Procedure 2: Catalytic Asymmetric Arninohydroxylation in 1:1 Tertbutanol/water (Used for Synthesis of Compounds 2,7 or 8)

To a solution of (DHQ)2-PHAL (2.20 g, 2.80 mmol, 5 mol %) in t-BuOH (100 mL) and water (100 ml) in 500 mL Erlenmeyer or round-bottomed flask were added in order, desired olefin (56.0 mmol), Chloramine-T trihydrate (48.4 g, 0.168 mol, 3.0 eq) and $K_2OsO_2(OH)_4$ (0.824 g, 2.24 mmol, 4 mol %). The reaction flask was immersed in a room-temperature water bath and the slurry stirred for 2.5 hr. Over the course of the reaction, the color changed from brown to deep green and then back to yellow as the stilbene slurry became a hydroxysulfonamide slurry. The product was isolated by filtration and the crude solid was washed once with cold (ca 5° C.) 1:1 t-BuOH/$H_2O$(15 mL) to yield the product β-hydroxysulfonamide. In the case of product 7, 16.1 g of N-(p-toluenesulfonyl)-(1S,2S)-2-amino-1,2-diphenylethanol (7) (78% yield, 64% ee, pure by NMR and HPLC). Trituration of this product twice with ethyl acetate (2×15 mL) at room temperature in a sintered glass funnel gave enantiomerically pure 7 (10.3 g, 50% yield, >99% ee, mp 166–167° C.). See Sharpless, J. Org. Chem. 1994, 59, 5104 and Sharpless, J. Org. Chem. 1994, 59, 8302 for analogous solid-to-solid AD procedures.

Analysis of Enantiomeric Excesses for 2–9

Methyl cinnamate derivative 2: Chiralcel OG, 30% i-PrOH/hexane, 1 mL/min; 21.8 min (2S,3R), 28.3 min (2R,3S). Ethyl crotonate derivative 5: Chiralcel OD-H, 15% i-PrOH/hexane, 1 mL/min, 7.5 min (2S,3R), 13.4 min (2R,3S). Dimethyl fumarate derivative 6: Chiralcel OG, 30% i-PrOH/hexane, 1 mL/min, 16.7 min (2S,3S), 21.8 min (2R,3R). trans-Stilbene derivative 5 :Chiralcel OD-H, 15% i-PrOH/hexane, 1 mL/min, 16.2 min (1S,2S), 26.0 min (1R,2R). cis-Stilbene derivative 8: Chiralcel OD-H, 15% i-PrOH/hexane, 0.5 mL/min, 18.5 min (1S,2R), 22.1 min (1R,2S). Cyclohexene derivative 9: Chiralcel OG, 15% i-PrOH/hexane, 0.5 mL/min, 28.5 min (1S,2R), 34.4 min (1R,2S).

Correlation of the Absolute Configurations of 2–9

Methyl Cinnamate Derivative (2R,3S)-2

Authentic (2R,3S)-2 was synthesized from N-benzoyl-(2R,3S)-3-phenylisoserine methyl ester (Taxol C-13 side chain; synthesis provided from Collet et al, Ecole normal superiure de Lyon, private communication) [6N HCl, reflux (remove methyl ester and N-benzoyl); $SOCl_2$, methanol (esterification); TsCl, $K_2CO_3$, 1:1 acetone/water (N-sulfonylation)] [HPLC: vide supra].

Ethyl Crotonate Derivative (2R,3S)-5

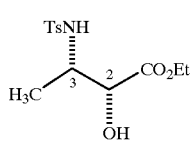

5

Compound 5:
(2R,3S)-5 was converted to N-tosyl-(2S)-alanine methyl ester [6N HCl (hydrolysis); $RuCl_3/H_5IO_6$ (oxidative cleavage); $SOCl_2$, methanol (esterification)] [HPLC: Chiralcel OD-H, 15% i-PrOH/hexane, 1 mL/min, 16.1 min (2R), 17.0 min (2S)].

Dimethyl Fumarate Derivative (2R,3R)-6

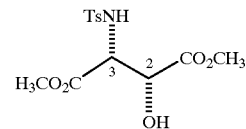

6

Compound 6:
(2R,3R)-6 was converted to its N-tosyl-(2R,3R)-2-oxazolidinone derivative which was independently synthesized from (1S,2S)-7 [carbonyl diimidazole, $CH_2Cl_2$; $RuCl_3$, $H_5IO_6$ (oxidative degradation of the phenyl groups);(Polt et. al. J. Org. Chem. 1992, 57, 5469), $SOCl_2$, methanol (esterification)] [HPLC: Chiralcel OD-H, 15% i-PrOH/hexane, 1 mL/min, 26.0 min (1R,2R), 47.2 min (1S,2S)].

Trans-Stilbene Derivative (1S,2S)-7

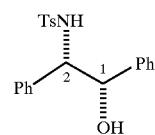

7

Compound 7:
An authentic sample of (1S,2S)-7 was synthesized from (1R,2S)-8 [$CrO_3$, $H_2SO_4$ (alcohol to ketone); DIBAL-H reduction gave a 4:1 mixture of (1R,2S)-8 to (1S,2S)-7] [HPLC: vide supra].

Cis-Stilbene Derivative (1S,2R)-8

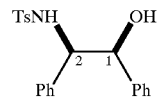

8

Compound 8:
An authentic sample of (1R,2S)-8 was synthesized from (1R,2S)-2-amino-1,2-diphenylethanol [TsCl, K2CO3, acetone/water] [HPLC: vide supra].

Cyclohexene Derivative (1S,2R)-9

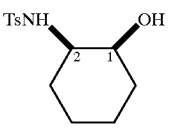

9

Compound 9:
N,N'-ditosyl-(1R,2R)-diaminocyclohexane was synthesized from (1S,2R)-7 [$SO_2Cl_2$, $Et_3N$, EtOAc; NaH (cyclic sulfamidate formation); $NaN_3$ (opening); $H_2$, Pd/C (azide reduction); TsCl, $K_2CO_3$, 1:1 acetone/water] and compared to the compound derived from authentic (1R,2R)-diaminocyclohexane [22] [HPLC: Chiralcel AS, 20% i-PrOH/hexane, 1 mL/min, 23.2 min (1R,2R), 32.3 min (1S,2S)].

Catalytic Asymmetric Aminohydroxylation in 1:1 Tertbutanol/Water (Used for Synthesis of Compounds 2, 13, 15, 23, 25 or 27)

Compounds 2, 13, 15, 23, 25 or 27

To a solution of $(DHQ)_2$-PHAL (2.20 g, 2.80 mmol, 5 mol %) in t-BuOH (100 mL) and water (100 ml) in 500 mL Erlenmeyer or round-bottomed flask were added in order, desired olefin (methyl cinnamate, p-methoxy-methyl-cinnamate 12, p-bromo-ethyl-cinnamate 14, o-methyl-methyl-cinnamate 22, 2,5-dimethyl-methyl-cinnamate 24 or 2,5-dimethoxy-methyl-cinnamate 26; all commercially available from Aldrich) (56.0 mmol), Chloramine-T trihydrate (48.4 g, 0.168 mol, 3.0 eq) and $K_2OsO_2(OH)_4$ (0.824 g, 2.24 mmol, 4 mol %). The reaction flask was immersed in a room-temperature water bath and the slurry stirred for 2.5 hr. Over the course of the reaction, the color changed from brown to deep green and then back to yellow as the stilbene slurry became a hydroxysulfonamide slurry. The product was isolated by filtration and the crude solid was washed once with cold (ca 5° C.) 1:1 t-BuOH/$H_2O$ (15 mL) to yield the product β-hydroxysulfonamide. Trituration of this product twice with ethyl acetate(2×15 mL) at room temperature in a sintered glass funnel gave enantiomerically pure β-hydroxysulfonamide compounds 2, 13, 15, 23, 25 or 27.

Catalytic Asymmetric Aminohydroxylation in 1:1:1 Ethanol/n-Propanol/Water (Used for Synthesis of Compound 11)

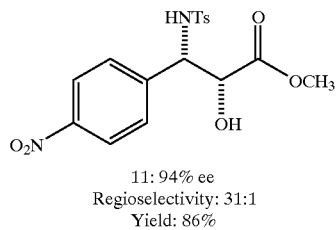

11: 94% ee
Regioselectivity: 31:1
Yield: 86%

To a solution of $(DHQ)_2$-PHAL (2.20 g, 2.80 mmol, 5 mol %) in ethanol (63 mL) n-Propanol (63 mL) and water (63 ml) in 500 mL Erlenmeyer or round-bottomed flask were added in order, commercially available p-nitro methyl cinnamate derivative (10; Aldrich chemical company) (9.08 g, 56.0 mmol), Chloramine-T trihydrate (48.4 g, 0.168 mol, 3.0 eq) and $K_2OsO_2(OH)_4$ (0.824 g, 2.24 mmol, 4 mol %). The reaction flask was immersed in a room-temperature water bath and the slurry stirred for 5 hr. Over the course of the reaction, the color changed from brown to deep green and then back to yellow as hydroxysulfonamide product appeared as white precipitates. The flask was then immersed in an ice bath (0° C.) for 20 min. During this cooling, almost all of crystalline hydroxysulfonamide product precipitated from the reaction solution. The product was isolated by filtration and the crude solid was washed once with cold (ca 5° C.) 1:1 n-Propanol/$H_2O$ (15 mL) to yield enantiomerically pure β-hydroxysulfonamide compound 11 in 86% overall yield and 94% ee.

Catalytic Asymmatric Aminohydroxylation in 1:1 n-Propanol/Water (Used for Synthesis of Compounds 17, 19, 21, 23 or 25)

Compounds 17, 19, 21, 23 or 25

To a solution of $(DHQ)_2$-PHAL (2.20 g, 2.80 mmol, 5 mol %) in n-Propanol (100 mL) and water (100 ml) in 500 mL Erlenmeyer or round-bottomed flask were added in order, commercially available methyl or ethyl cinnamate derivatives (16, 18, 20, 22 or 24; Aldrich chemical company) (9.08 g, 56.0 mmol), Chloramine-T trihydrate (48.4 g, 0.168 mol, 3.0 eq) and $K_2OsO_2(OH)_4$ (0.824 g, 2.24 mmol, 4 mol %). The reaction flask was immersed in a room-temperature water bath and the slurry stirred for 3 hr. Over the course of the reaction, the color changed from brown to deep green and then back to yellow as hydroxysulfonamide product appeared as white precipitates. The flask was then immersed in an ice bath (0° C.) for 20 min. During this cooling, almost all of crystalline hydroxysulfonamide product precipitated from the reaction solution. The product was isolated by filtration and the crude solid was washed once with cold (ca 5° C.) 1:1 n-Propanol/$H_2O$ (15 mL) to yield enantiomerically pure β-hydroxysulfonamide compounds 17, 19, 21, 23 or 25.

Preparation of Sulfonamides from Sulfonylchlorides

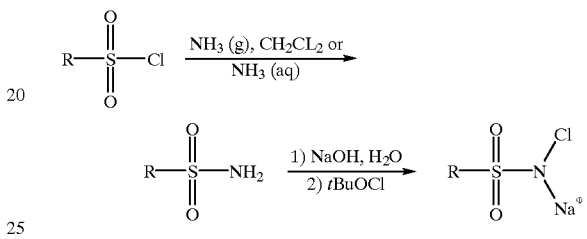

The sulfonyl chlorides used in the formation of the sulfonamides can come from commercially available sources such as Aldrich, Fluka, Sigma etc., or can be prepared from a procedure developed by Campbell et al. *Chem Rev.* 1978, 78, 65, for the preparation of N-chloro-N-sodiocarbamates which is a general procedure in the synthesis of N-chloro-N-sodio-aryl- and alkylsulfonamides. The sulfonyl chlorides (R—$SO_2$Cl) formed can include compounds where R=4-Me-Ph-, 4-MeOPh, Me, Ph-CH2-, 4-NO2-Ph-, 2-NO2-Ph-, 2-Naphthyl,1-Napthyl, Dansyl (FIGS. 9 and 12) or derivatives selected from the following functional groups:acyclic or cyclic hydrocarbons, hydroxyl compounds, ethers, protected amines, carbonyl compounds, esters or carboxylic acids, n-alkyl, alkynes (60) pyrans, pyrroles (54), various heterocycles including: nitriles (58), pyrazines, pyrazoles (55), pyridazines, pyridines (57),pyrimidines (59), pyrrolizines, quinazolines, quionlines, thiophenes, silanes, CHnX where X=$OR_1$, halogens, aromatic rings, heterocycles, silyl groups and n=1 to 2 (56) (FIG. 13).

Method A: Using a Sulfonyl Chloride (as Obtained Supra) and Gaseous $NH_{3(g)}$ $NH_3$ was bubbled (fritte or pipette) through well stirred $CH_2Cl_2$ (ca 100 ml) at RT. The sulfonyl chloride (100 mmol) was added in portions. After all of the sulfonyl chloride was added, stirring at RT under NH— was continued until TLC [hexane/ethylacetate] showed full conversion of the starting material. Precipitated NH4Cl was filtered off, the solvent was evaporated ($NH_3$) and the residue was crystallized from hot acetone/water and dried at high vaccum (oil pump, 0.1–0.01 torr) overnight to yield the crystalline, pure sulfonamides in nearly quantitative yields.

Method B: Using a Sulfonyl Chloride (as Obtained Supra) and Aqueous Ammonia

The sulfonylchloride (100 mmol) was added portionwise to a well stirred aqueous solution (100 ml) of NH3 (29.7%. Fisher) at RT. After all of the sulfonyl chloride was added, stirring at RT was continued for 2 more hours. The reaction mixture was slowly ($NH_3$!) heated to reflux and then cooled down to ca 4 C. The precipitated product was filtered off and crystallized from hot acetone/water and dried at high vaccum (oil pump, 0.1–0.01 torr) overnight to yield the crystalline, pure sulfonamides in nearly quantitative yields. Trimethylsilylethyl sulfonamide and related akylsilyl-sulfonamides can be prepared according to a literature procedure: Steven M. Weinreb et al. Tetrahedron Lett. 1986, 27, 2099–2102.

General Catalytic Asymmetric Aminohydroxylation by in Situ Generation of Chloramines Different from Chloramine T (in Situ Generation of R—SO$_2$NClNa)

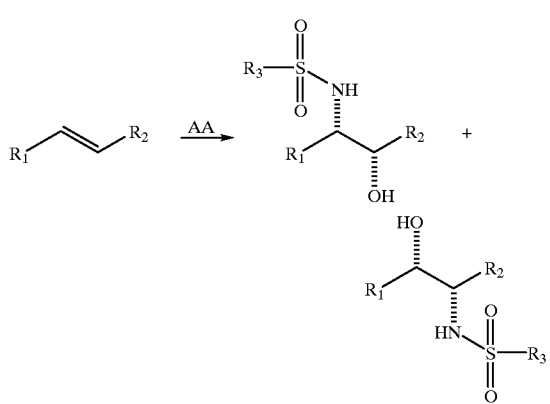

General Procedure

T-butyl hypochlorite was slowly added to a well stirred solution of the desired sulfonamide (as obtained vida supra; 3.1 mmol, 3.1 eq) and 122 mg (3.05 mmol. 3.05 eq) of NaOH in 7.5 ml of water at room temperature. After 10 more minutes of stirring this solution was added dropwise to a solution of 40 mg (0.05 mmol, 0.05 eq) of (DHQ)$_2$Phal or (DHQD)$_2$Phal in 7.5 ml of MeCN (alternatively, a 1:1 mix of t-BuOH/water, n-propanol/water or 1:1:1 ethanol/n-proanol/water can be used, depending upon optimization conditions). Subsequently 190 mg (1.0 mmol, 1.0 eq) of olefin where R$_1$=acyclic or cyclic hydrocarbons, heterocycles, hydroxyl compounds, ethers, protected amines, sulfides, carbonyl compounds, acrylates, substituted acrylates, esters or carboxylic acids.

R$_2$=combination of R$_1$.

R$_3$=4-Me-Ph-, 4-MeOPh, Me, Ph-CH2-, 4-NO2-Ph-, 2-NO2-Ph-, 2-Naphthyl,1-Napthyl, Dansyl or derivatives selected from the following functional groups: acyclic or cyclic hydrocarbons, hydroxyl compounds, ethers, protected amines,carbonyl compounds, esters or carboxylic acids, n-alkyl, pyrans, pyrroles, various heterocycles including: pyrazines, pyrazoles, pyridazines, pyridines, pyrimidines, pyrrolizines, quinazolines, quionlines, thiophenes, silanes, CHnX where X=OR$_1$, halogens, aromatic rings, heterocycles, silyl groups and n=1 to 2 (reagents commercially or synthetically available) and 14.7 mg (0.04 mmol, 0.04 eq) of K$_2$OsO$_2$(OH)$_4$ were added and the reaction mixture stirred at RT. After ca. 10 min all of the K$_2$OsO$_2$(OH)$_4$ was dissolved and the color of the reaction mixture turned to green. Stirring was continued until the green color of the reaction mixture had turned to yellow. 10 ml of aqueous Na$_2$SO$_3$ (sat.) were added to reduce excess Chloramine. The aqueous phase was separated and extracted three times with ca. 30 ml ethyl acetate. The combined organic phases were washed with brine containing 1% of NaOH, dried over MgSO$_4$ (anhydrous) and the solvent was evaporated in vaccu. The residue was purified by flash chromatography (SiO$_2$, hexane/ethyl acetate) to afford the pure crystalline aminohydroxylation product. In cases where regioisomeric products could be formed yields refer to a mixture of the two regioisomeres. Crystallization from ethyl acetate/hexane furnished the enantiomerically pure (>99% ee) N-aryl/alkylsulfonyl protected amino alcohol.

Catalytic Asymmetric Aminohydroxylation of Compounds 28–47 by in Situ Generation of Chloramines Different from Chloramine T (1 mmol Scale, in situ Generation of R—SO$_2$NClNa)

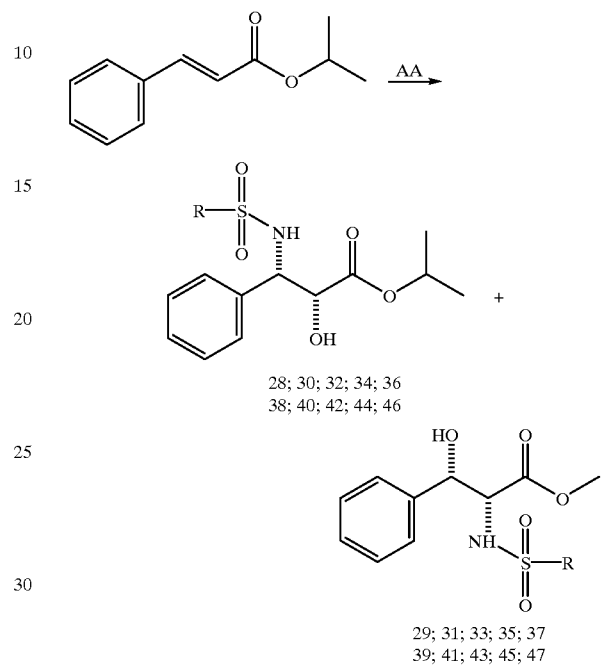

28; 30; 32; 34; 36
38; 40; 42; 44; 46

29; 31; 33; 35; 37
39; 41; 43; 45; 47

General Procedure

T-butyl hypochlorite was slowly added to a well stirred solution of the desired sulfonamide (as obtained vida supra; 3.1 mmol, 3.1 eq) and 122 mg (3.05 mmol. 3.05 eq) of NaOH in 7.5 ml of water at room temperature. After 10 more minutes of stirring this solution was added dropwise to a solution of 40 mg (0.05 mmol, 0.05 eq) of (DHQ)$_2$Phal or (DHQD)$_2$Phal in 7.5 ml of MeCN (alternatively, a 1:1 mix of t-BuOH/water, n-propanol/water or 1:1:1 ethanol/n-proanol/water can be used, depending upon optimization conditions). Subsequently 190 mg (1.0 mmol, 1.0 eq) of isopropyl cinnamate (commercially available from Aldrich) and 14.7 mg (0.04 mmol, 0.04 eq) of K$_2$OsO$_2$(OH)$_4$ were added and the reaction mixture stirred at RT. After ca. 10 min all of the K$_2$OsO$_2$(OH)$_4$ was dissolved and the color of the reaction mixture turned to green. Stirring was continued until the green color of the reaction mixture had turned to yellow.

10 ml of aqueous Na$_2$SO$_3$ (sat.) were added to reduce excess Chloramine. The aqueous phase was separated and extracted three times with ca. 30 ml ethyl acetate. The combined organic phases were washed with brine containing 1% of NaOH, dried over MgSO$_4$ (anhydrous) and the solvent was evaporated in vaccu. The residue was purified by flash chromatography (SiO$_2$, hexane/ethyl acetate) to afford the pure crystalline aminohydroxylation product. In cases where regioisomeric products could be formed yields refer to a mixture of the two regioisomeres. Crystallization from ethyl acetate/hexane furnished the enantiomerically pure (>99% ee) N-aryl/alkylsulfonyl protected amino alcohol.

Preparation of the Chloramine M: 48 (CH₃SO₂NCl)

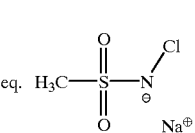

Chloramine M can be synthesized readily from methanesulfonamide (Aldrich chemical company) by addition of the stoichiometric amount of sodium hydroxide and t-butylhypochlorite in water or methanol. This method was adapted from a procedure developed by Campbell et al. Chem Rev. 1978, 78, 65, for the preparation of N-chloro-N-sodiocarbamates and proved to be general in the synthesis of N-chloro-N-sodio-aryl- and alkylsulfonamides. Chloramine M can be isolated either as a stable salt or can be prepared in situ, preferable in large scale syntheses.

Synthesis of Chloramine M

To an ice-cold stirred solution of 4.81 g (50 mmol) of methanesulfonamide and 2.0 g (50 mmol) sodium hydroxide in 40 mL of dry methanol is added very slowly 5.63 mL (5.4 g, 50 mmol) t-butylhypochlorite. The solution is stirred for 1 h and dried in vacuo to afford the pure N-chloro,N-sodio-methanesulfonamide in quantitative yield (7.58 g).

CH₃NSO₂NaCl, MW: 151.54; Elementary analysis: calcd.: C 7.93, H 2.00, N 9.24, Na 15.17, Cl 23.39 found: C 8.03, H 2.08, N 9.24, Na 15.36, Cl 23.12

For the in situ generation of Chloramine M the preparation can be done in the sufficient amount of water required for the AA reaction by using the same protocol.

General Procedure for Synthesis of Hydroxysufonamides Using Chloramine M (MeSO₂NClNa) on a 1 mmol Scale To a well stirred solution of 40 mg of (DHQD)₂PHAL (0.05 mmol, 0.05 eq) in 7.5 ml of n-propanol (alternatively, a 1:1 mix of t-BuOH/water, acetonitrile/water or 1:1:1 ethanol/n-proanol/water can be used, depending upon optimization conditions) was slowly added a solution of 455 mg (3.0 mmol, 3.0 eq) of MeSO₂NClNa in 7.5 ml of water, which resulted in a clear colorless solution. The substrate olefin (all commercially available from Aldrich, FIG. 15, 1.0 mmol, 1.0 eq ) and K₂OsO₂(OH)₄ (0.04 mmol, 0.04 eq) were subsequently added. Usually the reaction mixture turned green after some minutes and was stirred until color change to dark blue occurred (3–16 h), however colour changes are not generally observed. 10 ml of aqueous Na2SO3 (sat.) were added to reduce the excess MeSO2NClNa. The aqueous phase was separated and extracted three times with ca. 30 ml ethyl acetate. The combined organic phases were dried over MgSO4 (anhydrous) and the solvent was evaporated in vacuo.

To determine the exact yield the residue was purified by flash chromatography (SiO2, hexane/ethyl acetate) to afford the pure crystalline aminohydroxylation product. In cases where regioisomeric products can be formed yields refer to a mixture of the two regioisomeres. Crystallization from ethyl acetate/hexane furnished the enantiomerically pure (>99% ee) methane sulfonyl protected amino alcohol.

For preparative purposes work-up and purification can be simplified. As the methanesulfonamide is insoluble in CH2Cl2 and ether, but good soluble in aqueous solution (even in saturated aqueous NaCl solution) it can be removed extractively. It can also be crystallized out in CH₂Cl₂ or CH₂Cl₂/hexane mixtures. Alternatively it can be sublimed from the crude material at 80° C. Crystallization from ethyl acetate/hexane could usually furnish the chemically and enantiomerically pure (>99% ee) methane sulfonyl protected amino alcohol.

Asymmetric Aminohydroxylation in 1:1 Acetonitrile/Water

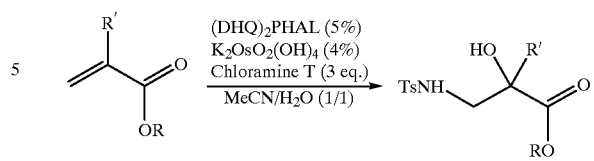

Figure 2:
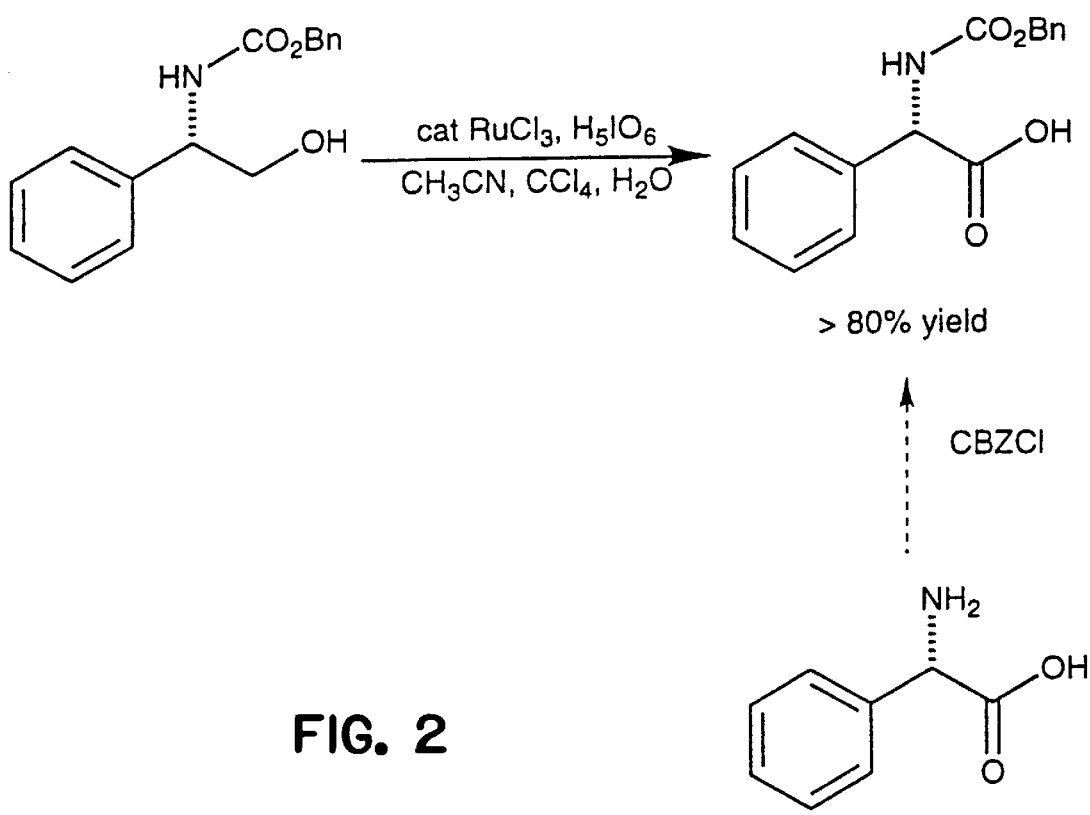
FIG. 2 illustrates the oxidation of the α-hydroxy-β-benzylcarbamate derived from styrene (see FIG. 1). Conditions include, but are not limited to: $RuCl_3$, $H_5IO_6$ oxidation to free acid: Sharpless et al *J. Org. Chem.* 3937 (46), 1981; $KMnO_4$/NaOH: Garner et al., Tetrahedron Lett., 5855–58, 1984; $RuO_2$: Martin, Tetrahedron Lett., 2701–02, 1988. $K_2CrO7/H_2SO_4$:J. Am Chem. Soc., 2498, 1960; PtO2: *J. Org. Chem.* 4898, 1987. If a tertbutylcarbamate is used in the asymmetric aminhydroxylation, the nitrogen is subsequently protected as a CBZ (carbobenzyloxy) group which can be independently obtained by protection of phenylalanine (dashed arrow).
Figure 3:
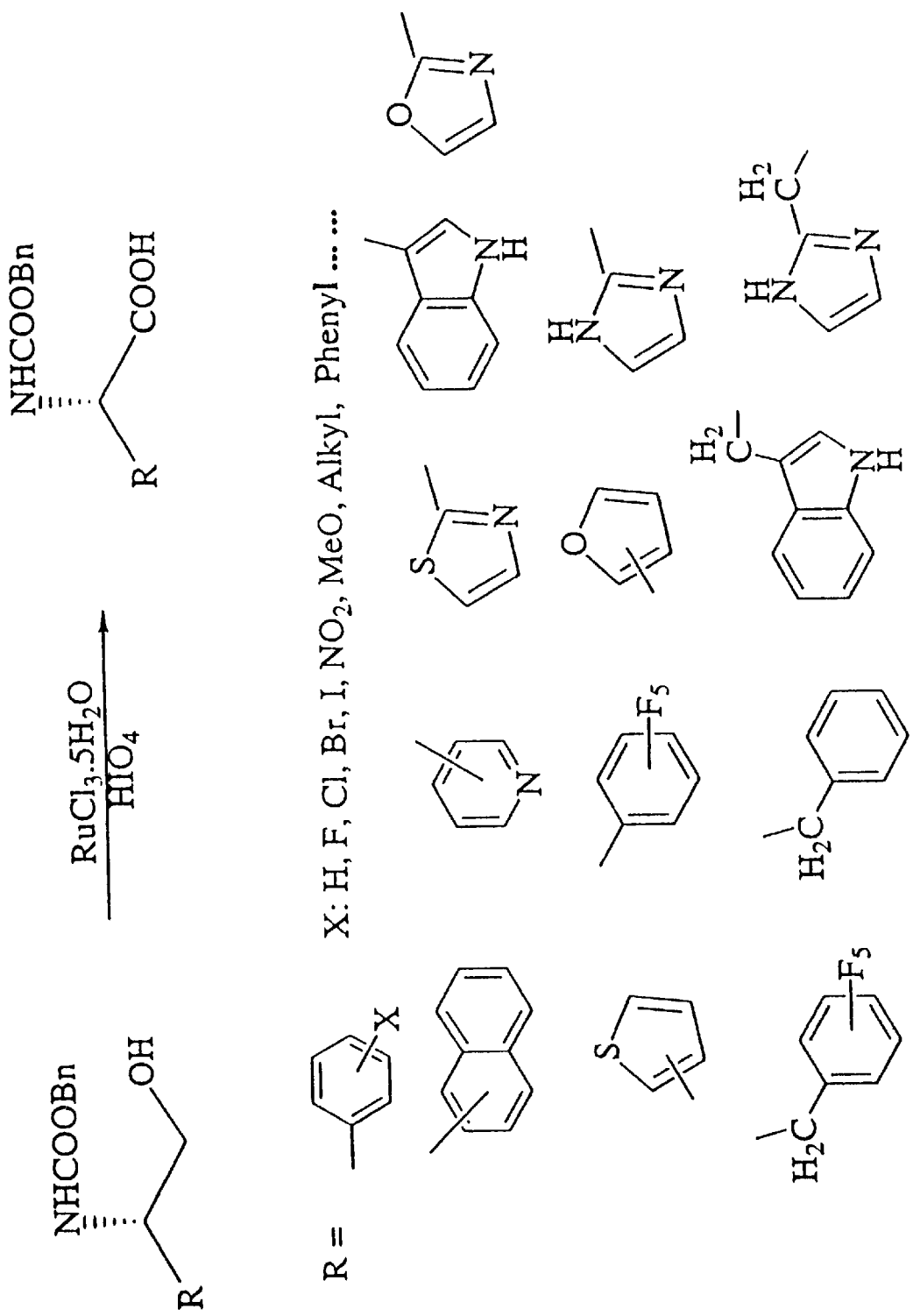
FIG. 3 illustrates oxidation conditions to the protected amino acid from the carbamate (benzyl carbamate is shown, however other carbamates commonly used in the AA procedure are possible) with indicated aromatic and heteroaromatic "R" groups.

To a stirred solution of (DHQ)₂-PHAL (0.11 g, 0.14 mmol, 5 mol %) in 20 mL of acetonitrile and 20 mL of water, in any convenient-sized glass vessel or vial, was added desired acrylate or methacrylates entries 1–10 (all commercially available from Aldrich, FIG. 16 and FIG. 17, 2.8 mmol), Chloramine-T trihydrate (2.42 g, 8.4 mmol, 3 eq) and K₂OsO₂(OH)₄ (41.6 mg, 0.112 mmol, 4 mol %). As the reaction proceeded to completion over the course of about one and half hours at room temperature, the color of the solution changed from yellow to pale green, then deep green and finally back to yellow. After addition of aqueous sodium sulfite (1.0 g in 15 mL H₂O ), the phases were separated, and the aqueous phase extracted with ethyl acetate (3×15 mL). The combined organic extracts were washed with brine, dried over MgSO₄ and the solvent concentrated to give the crude product, which also contains the p-toluenesulfonamide by-product produced upon the reduction of the excess Chloramine-T. Purification provides compounds as shown in FIG. 16, entries 1–10 with the indicated yields and conditions.

NOTE: Replacement of the 3 eq of Chloramine-T with 1.5 eq of Chloramine-T and 1.5 eq of Et₄NOAc gives comparable results and reduces the amount of p-toluenesulfonamide by-product formed. This can greatly simplify product isolation, especially in cases where the product and the toluenesulfonamide have similar chromatographic mobilities.

General Procedure for Synthesis of Compound 2

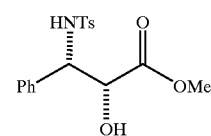

Compound 2

T-butyl hypochlorite was slowly added to a well stirred solution of the desired sulfonamide (as obtained vida supra; 3.1 mmol, 3.1 eq) and 122 mg (3.05 mmol. 3.05 eq) of NaOH in 7.5 ml of water at room temperature. After 10 more minutes of stirring this solution was added dropwise to a solution of 40 mg (0.05 mmol, 0.05 eq) of (DHQ)₂Phal or (DHQD)₂Phal in 7.5 ml of MeCN (alternatively, a 1:1 mix of t-BuOH/water, n-propanol/water or 1:1:1 ethanol/n-proanol/water can be used, depending upon optimization conditions).

Subsequently 190 mg (1.0 mmol, 1.0 eq) of methyl cinnamate (commercially available from Aldrich) and 14.7 mg (0.04 mmol, 0.04 eq) of K₂OsO₂(OH)₄ were added and the reaction mixture stirred at RT. After ca. 10 min all of the K₂OsO₂(OH)₄ was dissolved and the color of the reaction mixture turned to green. Stirring was continued until the green color of the reaction mixture had turned to yellow. 10 ml of aqueous Na₂SO₃ (sat.) were added to reduce excess Chloramine. The aqueous phase was separated and extracted three times with ca. 30 ml ethyl acetate. The combined organic phases were washed with brine containing 1% of NaOH, dried over MgSO$_4$ (anhydrous) and the solvent was evaporated in vaccu. The residue was purified by flash chromatography (SiO$_2$, hexane/ethyl acetate) to afford the pure crystalline aminohydroxylation product. In cases where regioisomeric products could be formed yields refer to a mixture of the two regioisomeres. Crystallization from ethyl acetate/hexane furnished the enantiomerically pure (>99% ee) N-aryl/alkylsulfonyl protected amino alcohol.

What is claimed is:

1. A method for converting an olefinic substrate to an asymmetric α-amino acid product, said asymmetric α-amino acid product being selected from a group consisting of amino acids and protected amino acids having a protected β-amino radical, the method comprising the following steps:

Step A: catalytically converting the olefinic substrate to a protected asymmetric β-aminohydroxide having a protected β-amino radical and a hydroxyl radical, said conversion employing a reaction solution which includes a source of the protected amino radical, an osmium compound as a catalyst, a chiral ligand for enantiomerically directing said asymmetric addition, and a solvent; then Step B: optionally deprotecting the protected amino radical of the protected asymmetric β-aminohydroxide of said Step A to form a deprotected asymmetric β-aminohydroxide;

Step C: oxidizing the hydroxyl radical of a first intermediate selected from the group consisting of the protected asymmetric β-aminohydroxide of said step A and the deprotected asymmetric β-aminohydroxide of said Step B to form the asymmetric α-amino acid product; and Step D: optionally deprotecting the protected amino radical of the protected amino acid to form the amino acid.

2. A method for converting an olefinic substrate to an asymmetric α-amino acid product as described in claim 1 wherein:

in said Step A: the source of the protected amino radical is a carbamate and the solvent has an organic component, the olefinic substrate and carbamate being present and soluble at a stoichiometric Molar concentration within the reaction solution, the osmium compound being present and soluble in catalytic amounts within the reaction solution, and the chiral ligand is present and soluble within the reaction solution at a Molar concentration within a range which is greater or equal to the catalytic Molar concentration of the osmium compound and less than stoichiometric Molar concentration of the olefinic substrate and carbamate.

3. A method for converting an olefinic substrate to an asymmetric α-amino acid product as described in claim 2, wherein:

in said Step A: the chiral ligand is present and soluble within the reaction solution at a concentration within a range approximately equivalent to the catalytic Molar concentration of the osmium compound.

4. A method for converting an olefinic substrate to an asymmetric α-amino acid product as described in claim 1 wherein:

in said Step A: the source of the protected amino radical is a carbamate and the solvent has an organic component, the olefinic substrate and carbamate being present and soluble at a stoichiometric concentration within the reaction solution, the osmium compound is present and soluble in catalytic amounts within the reaction solution, the solvent further including an aqueous component present at 10% or greater on a volume basis of the reaction solution; and the chiral ligand is present and soluble within the reaction solution at a Molar concentration which is approximately equivalent to the catalytic Molar concentration of the osmium and less than stoichiometric concentration of the olefinic substrate and carbamate.

5. A method for converting an olefinic substrate to an asymmetric α-amino acid product as described in claim 4, wherein:

in said Step A: the chiral ligand being present and soluble within the reaction solution at a Molar concentration within a range approximately equivalent to the catalytic Molar concentration of the osmium compound.

6. A method for converting an olefinic substrate to an asymmetric α-amino acid product as described in claim 1 wherein:

in said Step A: the source of the protected amino radical is a sulfonamide.

7. A method for converting an olefinic substrate to an asymmetric α-amino acid product, said asymmetric α-amino acid product being selected from a group consisting of amino acids and protected amino acids having a protected β-amino radical, the method comprising the following steps:

Step A: catalytically converting the olefinic substrate to a protected asymmetric β-aminohydroxide having a protected β-amino radical and a hydroxyl radical by means of catalytic asymmetric oxyamination reaction; then Step B: optionally deprotecting the protected β-amino radical of the protected asymmetric β-aminohydroxide of said Step A to form a deprotected asymmetric β-aminohydroxide;

Step C: oxidizing the hydroxyl radical of a first intermediate selected from the group consisting of the protected asymmetric β-aminohydroxide of said step A and the deprotected asymmetric β-aminohydroxide of said Step B to form the asymmetric α-amino acid product; and Step D: optionally deprotecting the protected β-amino radical of the protected amino acid to form the amino acid.

8. A method for converting an olefinic substrate to an asymmetric α-amino acid as described in claim 7 wherein the catalytic asymmetric oxyamination reaction of said Step A includes a reaction solution with a source of the protected amino radical, an osmium compound as a catalyst, a chiral ligand, and a solvent.

9. A method for converting an olefinic substrate to an asymmetric α-amino acid as described in claim 8 wherein the chiral ligand is selected from the group consisting of monovalent cinchona alkaloids, hydroquinine 1,4-phthalazinediyl diether ((DHQ)$_2$PHAL), hydroquinidine 1,4-pthalazinediyl diether ((DHQD)$_2$PHAL), and hydroquinidine-p-chlorobenzoate.

10. A method for converting an olefinic substrate to an asymmetric α-amino acid as described in claim 9 wherein the chiral ligand is selected from the group consisting of hydroquinine 1,4-phthalazinediyl diether ((DHQ)$_2$PHAL) and hydroquinidine 1,4-pthalazinediyl diether ((DHQD)$_2$PHAL).

* * * * *

UNITED STATES PATENT AND TRADEMARK OFFICE
CERTIFICATE OF CORRECTION

PATENT NO : 5,994,583
DATED : November 30, 1999
INVENTOR(S) : Sharpless, et al.

It is certified that error appears in the above-identified patent and that said Letters Patent are hereby corrected as shown below:

In Column 1, line 4, please insert:

--This invention was made with government support under Contract Nos. GM37696, GM28485 and AI15136 by the National Institutes of Health. The government has certain rights in the invention.--

Signed and Sealed this

Twenty-fourth Day of April, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO. : 5,994,583
DATED : November 30, 1999
INVENTOR(S) : Sharpless et al.

It is certified that error appears in the above-identified patent and that said Letters Patent is hereby corrected as shown below:

<u>Column 1,</u>
Line 4, please insert therefor:
-- This invention was made with government support under Contract Nos. GM28384, GM37696, GM28485 and AI15136 by the National Institutes of Health. The government has certain rights in the invention. --

Signed and Sealed this

Second Day of April, 2002

*Attest:*

JAMES E. ROGAN
*Attesting Officer*     *Director of the United States Patent and Trademark Office*